United States Patent
De Dios et al.

(10) Patent No.: US 7,582,638 B2
(45) Date of Patent: Sep. 1, 2009

(54) PYRAZOLE-ISOQUINOLINE UREA DERIVATIVES AS P38 KINASE INHIBITORS

(75) Inventors: Alfonso De Dios, Carmel, IN (US); Cristina Garcia-Paredes, Alcobendas (Madrid) (ES); Beatriz López de Uralde Garmendia, Alcobendas (Madrid) (ES); Mary Margaret Mader, Fishers, IN (US); Mark Andrew Pobanz, Westfield, IN (US); Chuan Shih, Carmel, IN (US); Boyu Zhong, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 12/089,420

(22) PCT Filed: Oct. 23, 2006

(86) PCT No.: PCT/US2006/041266
§ 371 (c)(1),
(2), (4) Date: Apr. 7, 2008

(87) PCT Pub. No.: WO2007/053346
PCT Pub. Date: Oct. 5, 2007

(65) Prior Publication Data
US 2008/0275056 A1 Nov. 6, 2008

Related U.S. Application Data

(60) Provisional application No. 60/750,200, filed on Dec. 14, 2005, provisional application No. 60/821,964, filed on Aug. 10, 2006.

(30) Foreign Application Priority Data

Oct. 28, 2005 (EP) .................. 05380240
Apr. 26, 2006 (EP) .................. 06380097

(51) Int. Cl.
*A61K 31/4725* (2006.01)
*A61K 31/496* (2006.01)
*C07D 403/141* (2006.01)

(52) U.S. Cl. .................. 514/253.05; 514/309; 514/310; 544/363; 546/141; 546/143

(58) Field of Classification Search ........................ None
See application file for complete search history.

(56) References Cited

FOREIGN PATENT DOCUMENTS

| EP | 1 609 789 | 12/2005 |
| WO | WO 00/43384 | 7/2000 |
| WO | WO 2004/004720 | 1/2004 |

OTHER PUBLICATIONS

Regan, J., et al., Pyrazole urea-based inhibitors of p39 MAP kinase: from lead compound to clinical candidate, Journal of Medicinal Chemistry, American Chemical Society, Washington US, vol. 45, No. 14, May 25, 2002.

*Primary Examiner*—Emily Bernhardt
(74) *Attorney, Agent, or Firm*—Tina M Tucker; Tonya Combs

(57) ABSTRACT

The present invention provides kinase inhibitors of Formula (I) wherein R1, R2, and X are as described herein, or a pharmaceutically acceptable salt thereof.

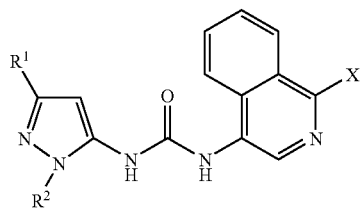

7 Claims, No Drawings

PYRAZOLE-ISOQUINOLINE UREA DERIVATIVES AS P38 KINASE INHIBITORS

This is the national phase application, under 35 USC 371, for PCT/US06/41266, filed Oct. 23, 2006, which claims the benefit under 35 USC 119(e) of U.S. Provisional Applications Nos. 60/750,200 filed Dec. 14, 2005 and 60/821,964 filed Aug. 10, 2006.

BACKGROUND OF THE INVENTION

The p38 kinase is a mitogen-activated protein (MAP) kinase that belongs to the serine/threonine kinase superfamily. This kinase is activated by extracellular stresses such as heat, UV light, and osmotic stress, as well as by inflammatory stimuli such as lipopolysaccharide. When activated, p38 kinase phosphorylates intracellular protein substrates that regulate the biosynthesis of the pro-inflammatory cytokines tumor necrosis factor α (TNFα) and interleukin-1β (IL-1β). These cytokines are implicated in the pathology of a number of chronic inflammatory disorders (Lee, et al., *Ann. N.Y. Acad. Sci.*, 696, 149-170 (1993); Muller-Ladner, *Curr. Opin. Rheumatol.*, 8, 210-220 (1996)), cardiovascular and central nervous system disorders (Salituro, et al., *Current Medicinal Chemistry*, 6, 807-823 (1999)), and autoimmune disorders (Pargellis, et al., *Nature Structural Biology*, 9(4), 268-272 (2002)). In addition, the phosphorylated form of mitogen-activated protein kinase-protein kinase 2 (or pMAPKAPK2) is also a kinase in the p38 MAPK pathway and can be directly activated by p38 MAPK. Mouse knockout studies of MAPKAPK2 show a reduction in cytokine production suggesting MAPKAPK2 can be a key regulator of the inflammatory response and can also be a potential target for anti-inflammatory therapy (WO 2005120509).

A number of urea compounds (for example in WO 9923091, WO 01012188, WO 04004720, WO 04037789, WO 99/32111, US 2004/0058961, EP 1609789, WO 03072569 and WO 0043384) have been identified as p38 kinase inhibitors or cytokine inhibitors. P38 kinase inhibitors or cytokine inhibitors may be costly to produce and may have bioavailability and absorption problems that limit the in vivo effects and therapeutic use. Therefore a need exists for new small molecule cytokine suppressive drugs, i.e., compounds that are capable of inhibiting p38 kinase with improved potency and greater bioavailability.

The present invention provides new inhibitors of p38 kinase useful for the treatment of conditions resulting from excessive cytokine production.

BRIEF SUMMARY OF THE INVENTION

The present invention provides compounds of Formula I:

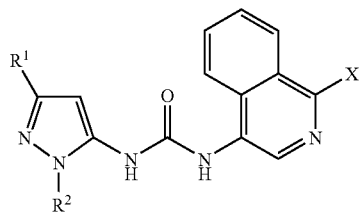

where:
X is selected from the group consisting of

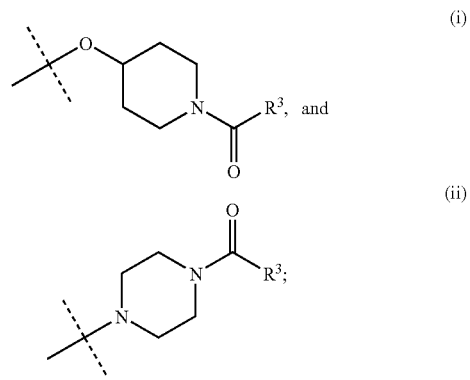

$R^1$ is $C_1$-$C_4$ alkyl, $C_3$-$C_4$ cycloalkyl optionally substituted with one or two substituents selected from the group of $C_1$-$C_4$ alkoxy, methyl, and trifluoromethyl; or $C_1$-$C_4$ alkylhalo;

$R^2$ is phenyl optionally substituted with $C_1$-$C_4$ alkyl, or pyridinyl optionally substituted with $C_1$-$C_4$ alkyl;

$R^3$ is amino, $C_1$-$C_4$ alkyl, $C_1$-$C_4$ alkoxy, $C_1$-$C_4$ alkylhalo, $C_3$-$C_4$ cycloalkyl optionally substituted with a substituent selected from methyl, trifluoromethyl, or halo; phenyl or thienyl each optionally substituted with a first substituent selected from the group consisting of: halo, $C_1$-$C_4$ alkyl, and $C_1$-$C_4$ alkoxy, and optionally further substituted with a second substituent selected from halo; or a pharmaceutically acceptable salt thereof.

The present invention also provides a method of inhibiting p38 kinase in a mammal comprising administering to a mammal in need of such treatment an effective amount of a compound of Formula I or a pharmaceutically acceptable salt thereof.

The present invention also provides a method of suppressing the production of tumor necrosis factor α (TNFα) in a mammal comprising administering to a mammal in need of such treatment an effective amount of a compound of Formula I or a pharmaceutically acceptable salt thereof.

The present invention also provides a method of suppressing the production of interleukin-1β (IL-1β) in a mammal comprising administering to a mammal in need of such treatment an effective amount of a compound of Formula I or a pharmaceutically acceptable salt thereof.

The present invention further provides a method of treating conditions resulting from excessive cytokine production in a mammal comprising administering to a mammal in need of such treatment a cytokine-suppressing amount of a compound of Formula I or a pharmaceutically acceptable salt thereof.

The present invention also provides a method of inhibiting the growth of a susceptible neoplasm in a mammal comprising administering to a mammal in need of such treatment a p38 inhibiting amount of a compound of Formula I or a pharmaceutically acceptable salt thereof.

The present invention also provides a method of inhibiting metastasis in a mammal comprising administering to a mammal in need of such treatment a p38 inhibiting amount of a compound of Formula I or a pharmaceutically acceptable salt thereof.

The present invention also provides a method of treating rheumatoid arthritis in a mammal comprising administering to a mammal in need of such treatment a p38 inhibiting amount of a compound of Formula I a pharmaceutically acceptable salt thereof.

The present invention also provides a pharmaceutical formulation comprising a compound of Formula I or a pharmaceutically acceptable salt thereof, in combination with a pharmaceutically acceptable excipient, carrier, or diluent.

This invention also provides the use of a compound of Formula I or a pharmaceutically acceptable salt thereof for the manufacture of a medicament for the inhibition of p38 kinase. Additionally, this invention provides a compound of Formula I or a pharmaceutically acceptable salt thereof for use in the inhibition of p38 kinase in mammals. Furthermore, this invention provides a pharmaceutical composition adapted for the inhibition of p38 kinase comprising a compound of Formula I or a pharmaceutically acceptable salt thereof in combination with one or more pharmaceutically acceptable excipients, carriers, or diluents thereof.

This invention also provides the use of a compound of Formula I or a pharmaceutically acceptable salt thereof for the manufacture of a medicament for the suppression of the production of tumor necrosis factor α (TNFα). Additionally, this invention provides a compound of Formula I or a pharmaceutically acceptable salt thereof for use in the suppression of the production of tumor necrosis factor α (TNFα) in mammals. Furthermore, this invention provides a pharmaceutical composition adapted for the suppression of the production of tumor necrosis factor α (TNFα) comprising a compound of Formula I or a pharmaceutically acceptable salt thereof in combination with one or more pharmaceutically acceptable excipients, carriers, or diluents.

This invention also provides the use of a compound of Formula I or a pharmaceutically acceptable salt thereof for the manufacture of a medicament for the suppression of the production of interleukin-1β (IL-1β). Additionally, this invention provides a compound of Formula I or a pharmaceutically acceptable salt thereof for use in the suppression of the production of interleukin-1β (IL-1β) in mammals. Furthermore, this invention provides a pharmaceutical composition adapted for the suppression of the production of interleukin-1β (IL-1β) comprising a compound of Formula I, or a pharmaceutically acceptable salt thereof, in combination with one or more pharmaceutically acceptable excipients, carriers, or diluents.

This invention also provides the use of a compound of Formula I or a pharmaceutically acceptable salt thereof for the manufacture of a medicament for the treatment of conditions resulting from excessive cytokine production. Additionally, this invention provides a compound of Formula I or a pharmaceutically acceptable salt thereof for use in the treatment of conditions resulting from excessive cytokine production in mammals. Furthermore, this invention provides a pharmaceutical composition adapted for the treatment of conditions resulting from excessive cytokine production comprising a compound of Formula I or a pharmaceutically acceptable salt thereof in combination with one or more pharmaceutically acceptable excipients, carriers, or diluents.

This invention also provides the use of a compound of Formula I or a pharmaceutically acceptable salt thereof for the manufacture of a medicament for the inhibition of growth of a susceptible neoplasm. Additionally, this invention provides a compound of Formula I or a pharmaceutically acceptable salt thereof for use in the inhibition of growth of a susceptible neoplasm in mammals. Furthermore, this invention provides a pharmaceutical composition adapted for the inhibition of growth of a susceptible neoplasm comprising a compound of Formula I or a pharmaceutically acceptable salt thereof in combination with one or more pharmaceutically acceptable excipients, carriers, or diluents.

This invention also provides the use of a compound of Formula I or a pharmaceutically acceptable salt thereof for the manufacture of a medicament for the inhibition of metastasis. Additionally, this invention provides a compound of Formula I or a pharmaceutically acceptable salt thereof for use in the inhibition of metastasis in mammals. Furthermore, this invention provides a pharmaceutical composition adapted for the inhibition of metastasis comprising a compound of Formula I or a pharmaceutically acceptable salt thereof in combination with one or more pharmaceutically acceptable excipients, carriers, or diluents.

This invention also provides the use of a compound of Formula I or a pharmaceutically acceptable salt thereof for the manufacture of a medicament for the treatment of rheumatoid arthritis. Additionally, this invention provides a compound of Formula I or a pharmaceutically acceptable salt thereof for use in the treatment of rheumatoid arthritis in mammals. Furthermore, this invention provides a pharmaceutical composition adapted for the treatment of rheumatoid arthritis comprising a compound of Formula I or a pharmaceutically acceptable salt thereof in combination with one or more pharmaceutically acceptable excipients, carriers, or diluents.

DETAILED DESCRIPTION OF THE INVENTION

The term "p38 kinase" is taken to mean the p38α and/or p38β kinase isoforms.

The term "suppressing the production of TNFα (IL-1β, cytokine)" is taken to mean decreasing of excessive in vivo levels of TNFα, IL-1β, or another cytokine in a mammal to normal or sub-normal levels. This may be accomplished by inhibition of the in vivo release of TNFα, IL-1β, or another cytokine by all cells, including macrophages; by down regulation, at the genomic level, of excessive in vivo levels of TNFα, IL-1β, or another cytokine in a mammal to normal or sub-normal levels; by inhibition of the synthesis of TNFα, IL-1β, or another cytokine as a posttranslational event; or by a down regulation of TNFα, IL-1β, or another cytokine at the translational level.

It will be understood by the skilled reader that the compounds of the present invention are capable of forming acid addition salts. In all cases, the pharmaceutically acceptable salts of all of the compounds are included in the names of them. Compounds of the present invention are amines, and accordingly will react with any of a number of inorganic and organic acids to form pharmaceutically acceptable acid addition salts. The term "pharmaceutically acceptable salt" as used herein, refers to salts of the compounds of Formula I which are substantially non-toxic to living organisms. Typical pharmaceutically acceptable salts include those salts prepared by reaction of the compounds of the present invention with a pharmaceutically acceptable organic or inorganic acids. Such salts include the pharmaceutically acceptable salts listed in *Journal of Pharmaceutical Science*, 66, 2-19 (1977), which are known to the skilled artisan. Mesylate salts of compounds of Formula I are most preferred.

Compounds of Formula I are inhibitors of p38 kinase. Thus, the present invention also provides a method of inhibiting p38 kinase in a mammal that comprises administering to a mammal in need of said treatment a p38 kinase-inhibiting amount of a compound of Formula I. It is preferred that the mammal to be treated by the administration of the compounds of Formula I is human.

As inhibitors of p38 kinase, compounds of the present invention are useful for suppressing the production of the pro-inflammatory cytokines tumor necrosis factor α (TNFα) and interleukin-1β (IL-1β), and therefore for the treatment of disorders resulting from excessive cytokine production. The present compounds are therefore believed to be useful in treating inflammatory disorders, including eczema, atopic dermatitis, rheumatoid arthritis, osteoarthritis, inflammatory bowel disease, and toxic shock syndrome. Compounds of the present invention are also believed to be useful in the treatment of cardiovascular disorders, such as acute myocardial infarction, chronic heart failure, atherosclerosis, viral myocarditis, cardiac allograft rejection, and sepsis-associated cardiac dysfunction. Furthermore, compounds of the present invention are also believed to be useful for the treatment of central nervous system disorders, such as meningococcal meningitis, Alzheimer's disease, Parkinson's disease, and multiple sclerosis. WO 99/32111, WO 9923091, WO 04004720, WO 03072569.

Most solid tumors increase in mass through the proliferation of malignant cells and stromal cells, including endothelial cells. In order for a tumor to grow larger than 2-3 millimeters in diameter, it must form a vasculature, a process known as angiogenesis. Suppression of tumor-induced angiogenesis by angiostatin and endostatin has been reported to result in antitumor activity (O'Reilly, et al., *Cell*, 88, 277-285 (1997)). The selective p38 kinase inhibitor SB22025 has been shown to inhibit angiogenesis (J. R. Jackson, et al., *J. Pharmacol. Exp. Therapeutics*, 284, 687 (1998)). Because angiogenesis is a critical component of the mass expansion of most solid tumors, the development of new p38 kinase inhibitors for the inhibition of this process represents a promising approach for antitumor therapy. This approach to antitumor therapy may lack the toxic side effects or drug resistance-inducing properties of conventional chemotherapy (Judah Folkman, *Endogenous Inhibitors of Angiogenesis*, The Harvey Lectures, Series 92, pages 65-82, Wiley-Liss Inc., (1998)).

As inhibitors of p38 kinase, compounds of the present invention, therefore, are also useful in inhibiting growth of susceptible neoplasms. Schultz, R. M. *Potential of p38 MAP kinase inhibitors in the treatment of cancer*. In: E. Jucker (ed.), *Progress in Drug Research*, 60, 59-92, (2003). A susceptible neoplasm is defined to be a neoplasm that depends upon p38 kinase for its survival, growth, or metastasis. Susceptible neoplasms include tumors of the brain, genitourinary tract, lymphatic system, stomach, larynx, and lung (U.S. Pat. No. 5,717,100). Preferably, the term "susceptible neoplasms" as used in the present application includes human cancers including non-small cell lung carcinoma (A. Greenberg, et al., *Am. J. Respir. Cell Mol. Biol.*, 26, 558 (2002)), breast carcinoma (J. Chen, et al., *J. Biol. Chem.*, 276, 47901 (2001); B. Salh, et al., *Int. J. Cancer*, 98, 148 (2002); and S. Xiong, et al., *Cancer Res.*, 61, 1727 (2001)), gastric carcinoma (Y. D. Jung, et al., *Proc. Am. Assoc. Cancer Res.*, 43, 9 (2002)), colorectal carcinomas (S. Xiong, et al., *Cancer Res.*, 61, 1727 (2001)), and malignant melanoma (C. Denkert, et al., *Clin. Exp. Metastasis*, 19, 79 (2002)).

Inhibition of angiogenesis by suppression of TNFα has also been taught to be useful in the inhibition or prevention of metastasis (U.S. Pat. No. 6,414,150; U.S. Pat. No. 6,335,336). Furthermore, suppression of TNFα is indicated for the treatment and prevention of cachexia, a wasting syndrome experienced by about half of all cancer patients (T. Yoneda, et al., *J. Clin. Invest.*, 87, 977 (1991)).

Furthermore, inhibition of p38 kinase may be effective in the treatment of certain viral conditions such as influenza (K. Kujime, et al., *J. Immunology.*, 164, 3222-3228 (2000)), rhinovirus (S. Griego, et al. *J. Immunology*, 165, 5211-5220 (2000)), and HIV (L. Shapiro, et al., *Proc. Natl. Acad. Sci. USA*, 95, 7422-7426, (1998)).

As used herein the term "$C_1$-$C_4$ alkyl" refers to a straight or branched, monovalent, saturated aliphatic chain of one to four carbon atoms and includes, but is not limited to, methyl, ethyl, propyl, isopropyl, butyl, isobutyl, and tert-butyl.

As used herein the term "$C_1$-$C_4$ alkoxy" refers to a straight or branched alkyl chain having from one to four carbon atoms attached to an oxygen atom. Typical $C_1$-$C_4$ alkoxy groups include methoxy, ethoxy, propoxy, isopropoxy, butoxy, tert-butoxy and the like. The term "$C_1$-$C_4$ alkoxy" includes within its definition the term "$C_1$-$C_3$ alkoxy".

As used herein the term "halo" refers to a chlorine, bromine, iodine or fluorine atom, unless otherwise specified herein.

As used herein the term "$C_1$-$C_4$ alkylhalo" refers to a $C_1$-$C_4$ alkyl substituted with up to five halo atoms. Typical $C_1$-$C_4$ alkylhalo groups include methylhalo, trifluoromethyl, ethylhalo, bisfluoromethyl ethyl, propylhalo, isopropylhalo, butylhalo, tert-butylhalo and the like. The term "$C_1$-$C_4$ alkylhalo" includes within its definition the term "$C_1$-$C_3$ alkylhalo".

As used herein the term "$C_3$-$C_4$ cycloalkyl" means a non-aromatic ring comprising carbon and hydrogen atoms and includes cyclopropyl and cyclobutyl.

As used herein the term "1-methyl-1-cyclopropyl" refers to the following residue:

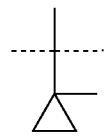

Certain classes of compounds of Formula I are preferred p38 kinase inhibitors. The following paragraphs describe such preferred classes:

a) X is

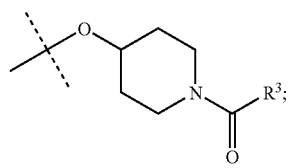

b) $R^1$ is $C_3$-$C_4$ cycloalkyl optionally substituted with a substituent selected from methyl, trifluoromethyl, or halo;

c) $R^1$ is 1-methyl-1-cyclopropyl;

d) $R^1$ is 2-fluoro-1,1-dimethyl-ethyl;

e) $R^1$ is 2-fluoro-1-fluoromethyl-1-methyl-ethyl;

f) $R^2$ is phenyl optionally substituted with methyl or pyridinyl optionally substituted with methyl;

g) $R^2$ is 4-tolyl;

h) $R^3$ is $C_3$-$C_4$ cycloalkyl optionally substituted with $C_1$-$C_4$ alkyl; or thienyl optionally substituted with methyl; or phenyl optionally substituted with a first substituent selected from the group consisting of: halo, $C_1$-$C_4$ alkyl, or $C_1$-$C_4$ alkoxy, optionally further substituted a halo substituent;

i) The compound of Formula I is a free base;

j) The compound of Formula I is a salt;

k) The compound of Formula I is the mesylate salt.

Preferred embodiments of the invention include all combinations of paragraphs a)-k). Other preferred compounds of Formula I are those where X is $R^1$ is as described in paragraph c); and $R^2$ is as described in paragraph g).

It is also preferred that X is $R^1$ is as described in paragraph c); and $R^2$ is as described in paragraph g); and $R^3$ is as described in paragraph h).

It is particularly preferred that X is $R^2$ is phenyl substituted in the 4-position with $C_1$-$C_4$ alkyl.

It is most preferred that X is

The following compound is also most especially preferred:

1-{1-[1-(1-Methyl-cyclopropanecarbonyl)-piperidin-4-yloxy]-isoquinolin-4-yl}-3-[5-(1-methyl-cyclopropyl)-2-p-tolyl-2H-pyrazol-3-yl]-urea The compounds of the present invention may be prepared by a variety of procedures, some of which are illustrated in the Schemes below. It will be recognized by one of skill in the art that the individual steps in the following schemes may be varied to provide the compounds of Formula I. The particular order of steps required to produce the compounds of Formula I is dependent upon the particular compound being synthesized, the starting compound, and the relative lability of the substituted moieties. Some substituents have been eliminated in the following schemes for the sake of clarity and are not intended to limit the teaching of the schemes in any way.

Compounds of Formula I and intermediates thereof may be prepared as illustrated in the following scheme wherein $R^1$, $R^2$, and X are as previously defined:

SCHEME 1

Formula I

Amine (a) is reacted with an appropriate isocyanate or carbamate, such as pyrazolyl-2,2,2-trichloroethyl carbamate, to provide compounds of Formula I. For example, a solution of the amine (1 equiv.), trichloroethyl carbamate (1 equiv.) and a suitable base such as diisopropylethylamine (2 equiv.), or potassium carbonate, in a suitable solvent, such as acetonitrile or dimethylsulfoxide (DMSO) is heated. The desired compound may then be isolated and, if necessary and desired, purified using techniques well known in the art, such as chromatography, to provide the compound of Formula I.

The requisite amines are prepared as illustrated below in Scheme 2 wherein X is as previously defined:

SCHEME 2

The nitro moiety (b) is reduced under standard reducing conditions, for example with hydrogen in the presence of a palladium catalyst, in a suitable solvent such as lower alkanols, or ethyl acetate, to provide the corresponding amine (a). Such reduction steps are well known and appreciated in the art. See Larock, R., "*Comprehensive Organic Transformations,*" 412, VCH Publishing, Inc., New York, 1989.

The requisite nitro compounds are prepared as illustrated in Scheme 3 below, wherein $R^3$ is as previously defined, and X' is $C(O)R^3$ or a suitable protecting group PG:

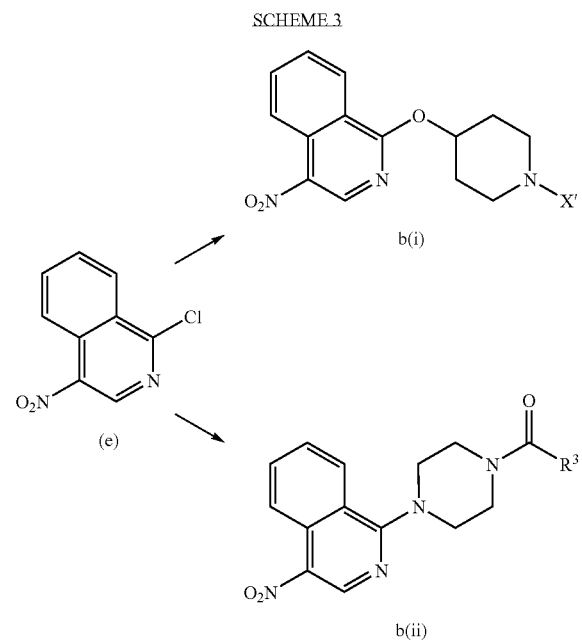

1-chloro-4-nitro-isoquinoline (e) in a suitable organic solvent, such as THF is reacted with an N-protected (PG) hydroxypiperidine and sodium hydride to provide the corresponding substituted piperidine b(i). A suitable amino protecting group "Pg", such as a tert-butoxycarbonyl (BOC) moiety, may be utilized if necessary or desired. Techniques for the introduction of these groups are well known to the skilled artisan. The skilled artisan will appreciate that the nitrogen-protecting groups may be removed at any convenient point in the synthesis of the compounds of the present invention. Methods of removing an amino-protecting group are well known in the art (for example, see: T. W. Greene, "*Protective Groups in Organic Synthesis*," John Wiley and Sons, New York, N.Y., 1999).

Alternatively, 1-chloro-4-nitro-isoquinoline (e) is reacted with the N-BOC protected piperazine in potassium carbonate in a polar solvent, such as acetonitrile, to provide the corresponding substituted piperazine b(ii).

The required pyrazolyl carbamates may be prepared as described in the following scheme, where $R^1$ and $R^2$ are as previously defined:

SCHEME 4

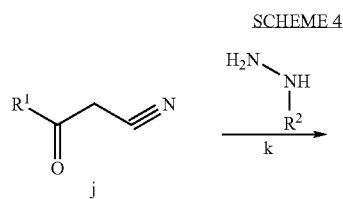

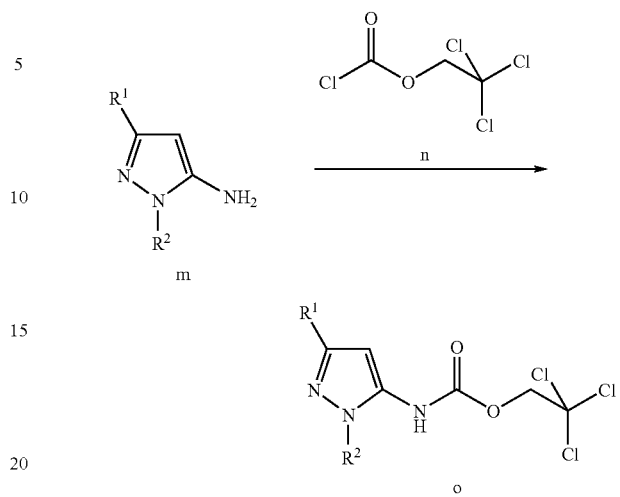

3-aminopyrazoles (m) are formed through conditions well known in the art; Larock, R., "*Comprehensive Organic Transformations,*" 79, VCH Publishing, Inc., New York, 1989. For example, an α-cyanoketone (j) and a suitable hydrazine or hydrazine salt (k) in a suitable organic solvent, such as ethanol, are reacted at an elevated temperature and may be purified using standard techniques, such as chromatography on a silica gel column.

2,2,2-Trichloroethyl chloroformate (n) is reacted with an appropriately substituted 3-aminopyrazole (m) and a base, for example sodium carbonate, in a suitable solvent, e.g., THF, to provide the corresponding 2,2,2-trichloroethyl carbamate (o). The skilled artisan will appreciate that the corresponding carbamate may be prepared by reacting the 3-aminopyrazole with other active carbonates.

Compounds of Formula I(i) may be prepared as demonstrated in Scheme 5 below wherein $R^1$, $R^2$, $R^3$, and PG are as previously defined:

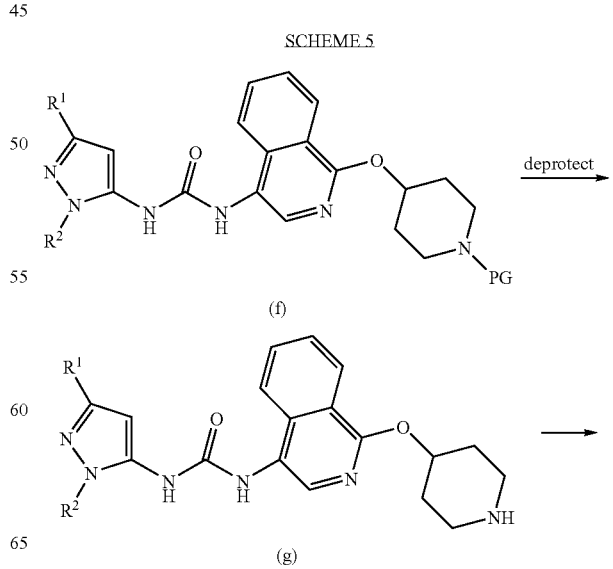

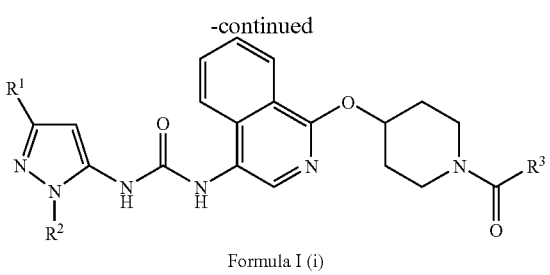

Formula I (i)

The compound of Formula (f) is deprotected under conditions well known in the art. For example, when the protecting group is tert-butoxy carbonyl, a compound of Formula (f) is dissolved in a suitable organic solvent or solvent mixture, such as dichloromethane, and treated with an acid, such as hydrochloric acid in dioxane or trifluoroacetic acid. Deprotection of N-protected-piperidine substituted urea (f) provides the substituted piperidine (g), which is reacted with a substituted carboxylic acid under the standard coupling conditions for organic acids and organic amines in the presence of a coupling agent, such as N-(3-dimethylaminopropyl)-N'-ethylcarbodiimide hydrochloride (EDCI), a catalytic amount of 4-dimethylaminopyridine (DMAP), and 1-hydroxybenzotriazole (HOBt), to provide Formula I (i). The skilled artisan will appreciate that examples of Formula I(i) may be prepared by beginning with other protected piperidines, including different N-protecting groups, such as formyl, which may require other deprotection procedures to form intermediate (g).

The skilled artisan will also appreciate that not all of the substituents in the compounds of Formula I will tolerate certain reaction conditions employed to synthesize the compounds. These moieties may be introduced at a convenient point in the synthesis, or may be protected and then deprotected as necessary or desired. The skilled artisan will appreciate that the protecting groups may be removed at any convenient point in the synthesis of the compounds of the present invention. Methods for introducing and removing nitrogen and oxygen protecting groups are well known in the art; see, for example, Greene and Wuts, *Protective Groups in Organic Synthesis*, John Wiley and Sons, New York, (1999). Furthermore, the skilled artisan will appreciate that in many circumstances, the order in which moieties are introduced is not critical. The particular order of steps required to produce the compounds of Formula I is dependent upon the particular compound being synthesized, the starting compound, and the relative lability of the substituted moieties.

The abbreviations, symbols and terms used in the examples and assays have the following meanings. AcOH=acetic acid, DCC=dicyclohexylcarbodiimide, DIEA=N,N-di-isopropyl-ethylamine, DMSO=dimethylsulfoxide, DMF=N,N-dimethylformamide, h=hour(s), HOBt=1-hydroxybenzotriazole, LDA=lithium diisopropylamide, EDCI=1-(3-dimethylaminopropyl)-3-ethylcarbodiimide hydrochloride, EtOAc=ethyl acetate, EtOH=ethanol, MeOH=methanol, NaBH(OAc)$_3$=sodium triacetoxyborohydride, TBAF=tetrabutyl ammonium fluoride, Tf$_2$O=trifluoromethanesuflonic anhydride, THF=tetrahydrofuran.

Preparation 1

1-Trifluoromethyl-cyclopronanecarboxylic Acid Methyl Ester

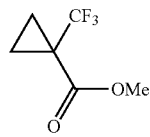

To a solution of 1-trifluoromethylcyclopropane-1-carboxylic acid (3.65 g, 23.7 mmol) in methanol-hexanes (2.5 mL-22.5 mL) add 2 M diazomethane solution in hexanes (14.2 mL, 28.45 mmol). Remove solvent under reduced pressure and distill the residue to give a yellow oil (2.93 g, 73% yield).

Preparation 2

3-(1-Methoxy-cyclopropyl)-3-oxo-propionitrile

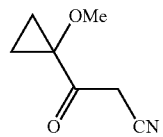

Add a solution of 2 M LDA in THF (29.1 mL, 58.3 mmol) to a dry ice-acetone cooled solution of 1-methoxy-cyclopropanecarboxylic acid methyl ester (WO2005/014577) (3.45 g, 26.5 mmol) and acetonitrile (2.17 g mL, 53.0 mmol) in THF (30 mL). Stir the reaction mixture at −78° C. for 1 hour and then at 22° C. for 0.5 hour. Evaporate the solvent to give a brown solid. Filter and wash with hexanes. Add 2N hydrochloric acid and extract three times with diethyl ether (50 mL each). Dry the combined organic phases over sodium sulfate. Removal of solvent provides a red oil (3.55 g, 96% yield, ES+(m/z) 140.1 [M+H]).

Prepare the following compounds in a manner substantially analogous to the procedure described above.

| Preparation | Compound |
| --- | --- |
| Preparation 3 | 4,4,5,5,5-Pentafluoro-3-oxo-pentanenitrile |
| Preparation 4 | 3-Oxo-3-(1-trifluoromethyl-cyclopropyl)-propionitrile |

Preparation 5

3-Hydroxy-2-hydroxymethyl-2-methyl-propionic Acid Methyl Ester

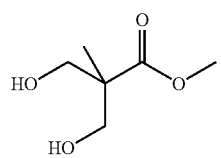

Add H$_2$SO$_4$ (4.5 g) to a suspension of 3-Hydroxy-2-hydroxymethyl-2-methyl-propionic acid (100 g) in MeOH (1 L, HPLC grade solvent) and stir at room temperature. for about 70 hours. Remove the solvent and partition the residue between EtOAc (1 L) and H₂O (100 mL). Re-extract the aqueous layer with EtOAc, and dry the combined organic fractions over MgSO₄. Filter and concentrate under reduced pressure. Crude mixture can be used without further purification. ¹H NMR (CDCl₃, 300 MHz): δ ppm 3.9 (d, 2H, J=11.1 Hz), 3.76 (s, 3H), 3.71 (d, 2H, J=11.1 Hz), 2.8 (bs, 2H), 1.1 (s, 3H)

Prepare the following compound in a manner substantially analogous to the procedure described above:

| Preparation | Compound |
| --- | --- |
| Preparation 6 | 3,3-Bis-hydroxymethyl-pentanoic acid ethyl ester |

Preparation 7

3-Hydroxy-2,2-dimethyl-propionic Acid Benzyl Ester

Add potassium hydroxide (486.7 mmol, 32.1 g) over a solution of 2,3-dihydroxy-2-methyl-propionic acid (423.2 mmol, 50 g) in 300 mL of DMF. Stir for 1 hour at 100° C. Then add benzyl bromide (584.04 mmol, 69.46 mL) and stir overnight. Cool down the mixture and dilute with ethyl acetate. Wash organic layer with water. Wash aqueous layer with ethyl acetate several times. Combine organic layers and dry over sodium sulfate, filter and concentrate under reduced pressure. ¹H NMR (CDCl₃, 300 MHz): δ ppm :7.36-7.32 (m, 5H), 5.1 (s, 2H), 3.5 (s, 2H), 1.21 (s, 6H).

Preparation 8

5-Pentafluoroethyl-2-p-tolyl-2H-pyrazol-3-ylamine

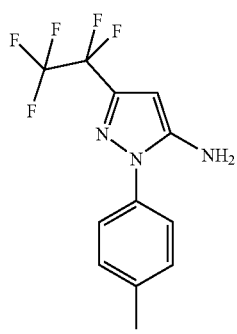

Heat a mixture of 4,4,5,5,5-pentafluoro-3-oxo-pentanenitrile (4 g, 21.4 mmol) and p-tolyl-hydrazine (10 g, 64.1 mmol) in ethanol (20 mL) to 95° C. in a sealed tube apparatus for 15 hours. After cooling to room temperature, remove the solvent under reduced pressure to give a brown residue. Subject residue to silica gel chromatography eluting with ethyl acetate and hexanes to give the title compound (3.24 g, 52% yield, ES+(m/z) 292.1 [M+H]).

Prepare the following compound in a manner substantially analogous to the procedure described above:

| Preparation | Compound | Data MS (ES+): m/z |
| --- | --- | --- |
| Preparation 9 | 2-p-Tolyl-5-(1-trifluoromethyl-cyclopropyl)-2H-pyrazol-3-ylamine | 282.3 [M + H] |

Preparation 10

5-(1-Fluoromethyl-cyclopropyl)-2-p-tolyl-2H-pyrazol-3-ylamine

Add AgF (4.5 eq, 4.56 g) to a solution of 1-fluoro-cyclobutanecarboxylic acid ethyl ester (1.6 g, 8 mmol) in acetonitrile 22 mL containing 274 mL of water. Heat the mixture at 80° C. in a sealed tube for 20 hours with vigorously stirring. Allow the mixture to cool and filter through Celite. Remove the solvent under reduced pressure to 1-fluoromethyl-cyclopropanecarboxylic acid ethyl estercompound as an oil (0.81 g, 61% yield). ES+(m/z) 147.1[M+1].

Stir i-Pr₂NH (1.7 mL, 2.2 eq, 12.1 mmol) and n-BuLi (1.6 M in hexanes, 7.5 mL, 2.2 eq, 12.1 mmol), in 12 mL of THF at −78° C. for 30 min under N₂, then add a solution of 1-fluoromethyl-cyclopropanecarboxylic acid ethyl ester (0.81 g, 5.5 mmol) in 7 mL of THF to the LDA solution. Stir and allow the mixture to warm from −78° C. to room temperature, then stir at room temperature for 5 hours. Add 10 mL of a saturated aqueous solution of NH₄Cl. Add AcOEt separate the organic layer, wash with a saturated aqueous sodium chloride solution, dry over Na₂SO₄ and remove solvent giving a brown oil (0.42 g, 54% yield). Dissolve compound in 10 mL of EtOH and add p-tolylhydrazine (0.47 g, 1 eq, 3 mmol). Heat the mixture in a sealed tube at 90° C. overnight. Then allow mixture to cool and remove solvent to give a residue. Purify by chromatography (hexane/AcOEt, 15-80%) to give title compound as an oil (0.336 g, 45% yield). ES+(m/z): 246.1 [M+1].

Preparation 11

5-(1-methoxy-cyclopropyl)-2-p-tolyl-2H-pyrazol-3-ylamine

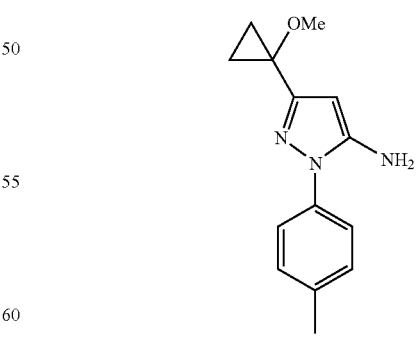

Heat a mixture of 3-(1-methoxy-cyclopropyl)-3-oxo-propionitrile (Preparation 2, 3.55 g, 25.5 mmol) and p-tolylhydrazine hydrochloride (12.15 g, 76.5 mmol) in ethanol (50 mL) at 90° C. in a sealed tube for 18 hours. After removal of the solvent, subject residue to silica gel chromatography eluting with 0-5% methanol in dichloromethane to give the title compound as a yellow solid (3.29 g, 53% yield, ES+(m/z) 244.2 [M+H]).

Prepare the following compounds in a manner substantially analogous to the procedure described above:

| Preparation | Compound | Data MS (ES+): m/z |
|---|---|---|
| Preparation 12 | 2-(6-Methyl-pyridin-3-yl)-5-(1-trifluoromethyl-cyclopropyl)-2H-pyrazol-3-ylamine | 283.2 [M + H] |

Preparation 13

[5-(1-Methoxy-cyclopropyl)-2-p-tolyl-2H-pyrazol-3-yl]carbamic acid 2,2,2-trichloro-ethyl ester

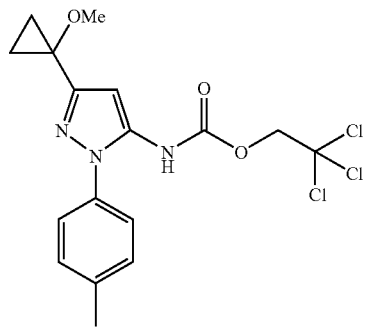

To an ice-salt cooled solution of 5-(1-methoxy-cyclopropyl)-2-p-tolyl-2H-pyrazol-3-ylamine (Preparation 11, 2.43 g, 10 mmol) and pyridine (0.9 mL, 11 mmol) in THF (30 mL), add a solution of 2,2,2-trichloroethylchloroformate (2.12 g, 10 mmol) in THF (10 mL) dropwise. Stir at −15° C. for 0.5 hour, then at 22° C. for 1 hour. Partition the reaction mixture between dichloromethane (50 mL) and saturated aq. sodium bicarbonate (50 mL). Isolate the aqueous phase and extract twice with dichloromethane (25 mL each). Dry the combined organic phases over sodium sulfate and concentrate. Subject residue to silica gel chromatography eluting with hexanes and ethyl acetate to give a white solid (3.73 g, 89% yield, ES+(m/z) 418.1 [M+H]).

Prepare the following compounds in a manner substantially analogous to the procedure described above:

| Preparation | Compound | Data MS (ES+): m/z |
|---|---|---|
| Preparation 14 | [2-p-Tolyl-5-(1-trifluoromethyl-cyclopropyl)-2H-pyrazol-3yl]-carbamic acid 2,2,2-trichloro-ethylester | 458.2 [M + H] |
| Preparation 15 | [2-(6-Methyl-pyridin-3-yl)-5-(1-trifluoromethyl-cyclopropyl)-2H-pyrazol-3-yl]-carbamic acid 2,2,2-trichloro-ethylester | 403.2 [M + H] |
| Preparation 16 | (5-Pentafluoromethyl-2-p-tolyl-2H-pyrazol-3-yl)-carbamic acid 2,2,2-trichloro-ethyl ester | 466.1 [M + H] |

Preparation 17

1-(5-tert-Butyl-2-p-tolyl-2H-pyrazol-3-yl)-carbamic acid 2,2,2-trichloro-ethyl ester To a solution of 5-tert-butyl-2-p-tolyl-2H-pyrazol-3-ylamine (Regan et al. J. Med. Chem. 2002, 45, 2994-3008, 400 g, 1.74 mol) in THF (8 L) add a saturated solution of sodium carbonate (2.4 L) and cool the mixture to 0° C. Then add 2,2,2-trichloroethyl chloroformate (406.77 g, 1.92 mol) dropwise and stir mixture at 0° C. for 2 hours. Extract the reaction mixture with ethyl acetate (3×6.5 L), dry over anhydrous magnesium sulfate and evaporate the solvent. Dissolve the solid in a minimum amount of ethyl acetate and add an excess of hexanes to precipitate the solid. Collect the solid by filtration and dry to obtain the title compound as an off white solid (586 g, 83% yield). (ES+): m/z 406.1 (M+H).

Preparation 18

[5-(1-Methyl-cyclopropyl)-2-p-tolyl-2H-pyrazol-3-yl]-carbamic acid 2,2,2-trichloro-ethyl ester

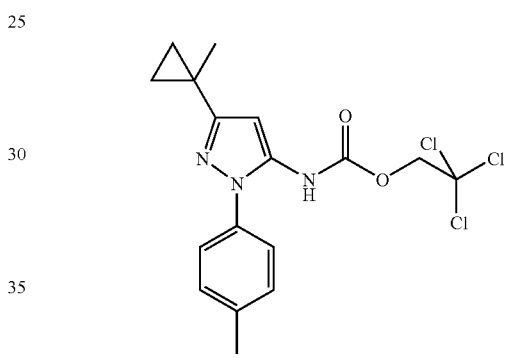

Add acetonitrile (87 mL, 1.6 mol) to a suspension of sodium hydride (66 g, 1.6 mol) in THF (700 mL) at room temperature and stir 10 minutes. Then add 1-methyl-cyclopropanecarboxylic acid methyl ester (90.0 g, 0.78 mol) and reflux the white slurry for 3 hours. Cool the mixture, then add methanol (200 mL) and pour the mixture over water (500 mL). Separate the phases and reduce the pH of the aqueous phase with 1.0N HCl until pH 3-4. Extract the aqueous phase with diethyl ether (2×350 mL), combine the organic layers and wash with aqueous sodium chloride. Dry over sodium sulfate, filter, and concentrate under reduced pressure to give 3-(1-methyl-cyclopropyl)-3-oxo-propionitrile as yellow oil. $^1$H NMR (CDCl$_3$): 3.59 (s, 2H), 1.37 (s, 3H), 1.30 (q, J=4 Hz, 2H), 0.86 (q, J=4 Hz, 2H).

Alternatively, to a 5 L three-necked round-bottom flask equipped with overhead stirrer, thermocouple, reflux condenser, and an addition funnel, add potassium tert-butoxide in THF (3.00 L, 3.00 moles). Mix 1-methyl-cyclopropanecarboxylic acid ethyl ester (264.00 g, 2.06 moles) with acetonitrile (123.00 g, 3.00 moles), then add through an addition funnel over 0.5 hour to the butoxide solution. Heat the resulting mixture to reflux. Reflux 2 hours, then cool to <40° C. by adding methanol (96.00 g, 3.00 mL). Stir the mixture 10 minutes, then transfer the contents to a 12 L separatory funnel containing a vigorously stirring mixture of water (3.96 L, 219.81 moles) and MTBE (3.96 L, 33.32 moles). Separate the layers and extract the aqueous layer with MTBE (3.96 L, 33.32 moles). Adjust the pH of the aqueous layer from 12.5 to 3.5 using 5 N HCl (610.00 mL, 3.05 moles). Extract the aqueous layer with MTBE (2×1.32 L, 11.11). Combine the organic layers, dry over sodium sulfate (62.00 g, 436.49 moles), and filter to afford 3-(1-methyl-cyclopropyl)-3-oxo-propionitrile.

Heat to reflux a solution of 3-(1-methyl-cyclopropyl)-3-oxo-propionitrile (60 g, 487.2 mmol) and p-tolyl-hydrazine hydrochloride (78 g, 478.2 mmol) in ethanol (975 mL) for 4 hours. Evaporate the solvent and dissolve the remaining solid in water. Increase pH of the solution to pH 8 using a 1.0 N solution of sodium hydroxide. Filter the precipitate to obtain 5-(1-methyl-cyclopropyl)-2-p-tolyl-2H-pyrazol-3-ylamine as a white solid. $^1$H NMR (DMSO): 7.39 (d, J=8 Hz, 2H), 7.22 (d, J=8 Hz, 2H), 5.12 (s, 2H), 2.31 (s, 3H), 1.30 (s, 3H), 0.80 (q, J=4 Hz, 2H), 0.61 (q, J=4 Hz, 2H).

Add dropwise 2,2,2-trichloroethyl chloroformate (3.0 mL, 23 mmol) to a solution of 5-(1-methyl-cyclopropyl) -2-p-tolyl-2H-pyrazol-3-ylamine (4.75 g, 21 mmol) in tetrahydrofuran (105 mL) and saturated aqueous sodium carbonate (32 mL) at 0° C. Stir at this temperature for 2 hours. Pour the mixture into water and separate phases. Extract the aqueous with ethyl acetate.

Work-Up A: Combine the organic layers and wash with aqueous sodium chloride, dry over sodium sulfate, filter, and concentrate under reduced pressure to give a yellow solid. Dissolve the solid in the minimum amount of ethyl acetate and add hexanes until cloudy while stirring. Crystallize the title compound and filter as a white solid. $^1$H NMR (DMSO): 9.89 (br s, 1H), 7.31 (d, J=8 Hz, 2H), 7.23 (d, J=8 Hz, 2H), 6.12 (s, 1H), 4.82 (s, 2H), 2.31 (s, 3H), 1.37 (s, 3H), 0.89 (q, J=4 Hz, 2H), 0.71 (q, J=4 Hz, 2H).

Work-Up B: Exchange the ethyl acetate solvent for isopropyl alcohol (91.56 moles). Stir the slurry at <0° C. for 2 hours, filter, wash with cold isopropyl alcohol (13.08 moles), and dry at 40° C. under reduced pressure overnight to afford the title compound, as a white crystalline solid Preparation 19

[5-(2-Fluoro-1-fluoromethyl-1-methyl-ethyl)-2-p-tolyl-2H-pyrazol-3-yl]-carbamic acid 2,2,2-trichloro-ethyl ester Add Tf$_2$O (80 mL) dropwise to a cool solution (−78° C.) of 3-hydroxy-2-hydroxymethyl-2-methyl-propionic acid methyl ester (Preparation 5, 32.5 g) in dichloromethane (400 mL) and 2,6-lutidine (80 mL). Allow the reaction to reach room temperature. and stir for about 2 hours. Dilute with dichloromethane (400 mL) and wash with HCl (3% aqueous solution). Dry the organic layer over MgSO$_4$, filter and concentrate. Subject residue to silica gel chromatography eluting with hexanes/ethyl acetate 5%, to give 2-methyl-2,3-bis-trifluoromethanesulfonyloxy-propionic acid methyl ester as a colorless oil. $^1$H NMR (CDCl$_3$, 300 MHz): δ ppm 4.7 (d, 2H, J=10.3 Hz), 4.5 (d, 2H, J=10.3 Hz), 3.8 (s, 3H), 1.4 (s, 3H).

Add TBAF 1M (132 mmol, 132 mL) over a solution of 2-Methyl-2,3-bis-trifluoromethanesulfonyloxy-propionic acid methyl ester (65.9 mmol, 26.3 g) in 500 mL of anhydrous THF cooled down to 0° C. Stir overnight. Concentrate under reduced pressure and add dichloromethane. Wash the organic layer with saturated aq. sodium chloride. Combine the organic layers and dry over sodium sulfate, filter, and concentrate under reduced pressure to give 3-fluoro-2-fluoromethyl-2-methyl-propionic acid methyl ester. $^1$H NMR (CDCl$_3$, 300 MHz): δ ppm: 4.7-4.4 (m, 4H), 3.5 (s, 3H), 0.98 (t, 3H, J=1.7 Hz)

Add LDA 2.0 M (62.0 mmol, 31 mL) followed by anhydrous acetonitrile (56.4 mmol, 2.9 mL) to a solution of 3-fluoro-2-fluoromethyl-2-methyl-propionic acid methyl ester (28.2 mmol, 4.3 g) in 100 mL of anhydrous THF cooled down to −78° C. Stir for 2 hours at −78° C. and allow the solution to warm to room temperature overnight. Concentrate under reduced pressure and add dichloromethane. Wash the organic layer with saturated aq. sodium chloride and aqueous 10% HCl. Combine the organic layers and dry over sodium sulfate, filter, and concentrate under reduced pressure to give a residue.

Stir p-tolylhydrazine hydrochloride (15.5 mmol, 2.5 g) and residue obtained above (15.5 mmol, 2.5 g) in 31 mL of ethanol at 90° C. overnight. Evaporate the solvent, and dissolve the residue in water. Add 10% sodium hydroxide solution, and extract in ethyl acetate. Combine the organic layers and dry over sodium sulfate, filter, and concentrate under reduced pressure to give 5-(2-fluoro-1-fluoromethyl-1-methyl-ethyl)-2-p-tolyl-2H-pyrazol-3-ylamine. Subject residue to silica gel chromatography eluting with hexanes/ethyl acetate as eluent (from 15% to 50%). LCMS ES+ (m/z) 266 [M+H]).

Add 2,2,2-trichloroethyl chloroformate (8.1 mmol, 1.1 mL) and aqueous sodium carbonate solution (4.8 mL) over a solution of 5-(2-fluoro-1-fluoromethyl-1-methyl-ethyl)-2-p-tolyl-2H-pyrazol-3-ylamine (7.3 mmol, 1.9 g) in 37 mL of THF. Stir for 24 hours. Pour the solution over water and extract in ethyl acetate. Combine organic layers and wash with saturated aq. sodium chloride. Dry over sodium sulfate, filter, and concentrate under reduced pressure to give [5-(2-fluoro-1-fluoromethyl-1-methyl-ethyl)-2-p-tolyl-2H-pyrazol-3-yl]-carbamic acid 2,2,2-trichloro-ethyl ester. LCMS ES+ (m/z) 440 [M+H].

Prepare the following compounds in a manner substantially analogous to the procedure set forth above.

| Preparation | Compound | Data MS (ES+): m/z [M + H] |
|---|---|---|
| Preparation 20 | [5-(1,1-Bis-fluoromethyl-propyl)-2-p-tolyl-2H-pyrazol-3-yl]-carbamic acid 2,2,2-trichloro-ethyl ester | 454 |
| Preparation 21 | [5-(2-Fluoro-1,1-dimethyl-ethyl)-2-p-tolyl-2H-pyrazol-3-yl]-carbamic acid 2,2,2-trichloro-ethyl ester | 424 |

Preparation 22

4-(4-amino-isoquinolin-1-yloxy)-piperidine-1-carboxylic acid tert-butyl ester

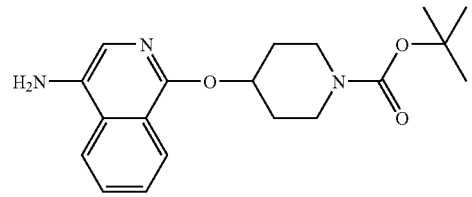

Cool sulfuric acid (900 mL) to 5° C. using an ice/acetone bath, then add 1-aminoisoquinoline (208.8 g, 1448 mmol) over 45 min keeping the internal temperature of the mixture <20° C. Cool the dark mixture to 0° C. under nitrogen with mechanical stirring then treat with KNO$_3$ (149.4 g, 1477 mmol) in portions over 45 min keeping the reaction mixture's temperature <10° C. Stir the mixture for 2 hours while warming to 15° C. Pour the mixture into water/ice (3 kg) then dilute with additional water (6 L). Stir the slurry for 45 min then filter. Wash the cake with water (6×1.5 L). Partially dry the golden material by air overnight then place in a vacuum oven (50-55° C., ca. 10 torr, nitrogen bleed, 24 h) to afford 1-amino-4-nitroisoquinoline H$_2$SO$_4$ (256.8 g, 62% yield). (ES+): m/z 190 (M$^+$+H).

Stir a slurry of 1-amino-4-nitroisoquinoline H$_2$SO$_4$ (120 g, 418 mmol) in aqueous HCl (6 N, 2 L) mechanically under nitrogen at 35° C. Add a solution of NaNO$_2$ (72.1 g, 1044 mmol) in water (300 mL) over 1 hour while warming the slurry to 50° C. Heat the mixture an additional 30 minutes then allow to cool to room temperature and stir overnight. Heat the mixture to 50° C., then add a solution of NaNO$_2$ (36 g in 150 mL of water) over 30 minutes. Stir the mixture for 2 hours then heat to 60° C., allow to cool slowly to room temperature over 3 hours. Filter the resulting slurry, and wash the cake with water (3×600 mL). Partially air-dry (180 g). Slurry the wet solid in i-PrOH (1 L) and EtOH (1 L) at reflux, add THF (350 mL) to effect complete dissolution. To the solution add water (400 mL), and cool to 10° C. over 3 hours. Filter and wash with EtOH (2×300 mL), then diethyl ether (3×150 mL). Air-dry overnight to afford 1-hydroxy-4-nitroisoquinoline (62.62 g, 79% yield) as a light brown solid. (ES+): m/z 191 (M$^+$+H).

Stir a slurry of 1-hydroxy-4-nitroisoquinoline (62.2 g, 327 mmol) in POCl$_3$ (180 mL) mechanically under nitrogen and heat to 100-105° C. for 1 hour resulting in a homogeneous dark brown solution. Exchange the condenser for a short-path distillation head, and remove excess POCl$_3$ under reduced pressure (ca. 10-30 torr) resulting in a pot temperature of 55° C. To this mixture add 1,2-dichloroethane (150 mL), and warm the mixture to 70° C. to obtain a homogeneous solution. Cool the solution to 15° C., then add i-PrOH (450 mL) over 5 minutes resulting in an exotherm to 33° C. Stir the slurry for 3.5 hours at 15° C. then filter and wash with i-PrOH (3×100 mL). Air-dry the resulting solid overnight to afford 1-chloro-4-nitroisoquinoline (52.08, 76% yield) as a tan solid. (ES+): m/z 209/211 (M$^+$+H).

Add NaH (60% in mineral oil, unwashed; 6.23 g, 156 mmol) in portions to a solution of 1-chloro-4-nitroisoquinoline (26.0 g, 125 mmol) and 1-tert-butoxycarbonyl-4-hydroxypiperidine (27.6 g, 137 mmol) in THF (350 mL) stirred at room temperature under nitrogen flow. Stir the dark reddish mixture at 40° C. for 1.5 hours then 55° C. for 1.5 hours. Add additional NaH (1.3 g), and stir the resulting mixture at 55° C. for 2 hours then cool to room temperature overnight. Add hexanes (75 mL), then add water (600 mL) slowly. Adjust the reaction mixture to pH 7 with aqueous HCl (1 N), then separate layers. Discard the aqueous layer and add hexanes (200 mL) to the organic layer. Partially concentrate the mixture under reduced pressure to a volume of 50-100 mL. Add diethyl ether (150 mL) and hexanes (250 mL), then filter the resultant slurry. Wash the cake with diethyl ether/hexanes (1:1) and air-dry to provide 4-(4-nitro-isoquinolin-1-yloxy)-piperidine-1-carboxylic acid tert-butyl ester (33.84 g, 73% yield) as a tan solid. (ES+): m/z 374 (M$^+$+H).

To a slurry of 4-(4-nitro-isoquinolin-1-yloxy)-piperidine-1-carboxylic acid tert-butyl ester (33.5 g, 89.7 mmol) in THF (300 mL) and ethanol (300 mL) add 10% Pd/C (1.80 g, 1.69 mmol) as a slurry in ethanol (25 mL). Place the mixture in a Parr shaker under hydrogen atmosphere (25-40 psi) at room temperature for 8 hours. Filter the mixture through a pad of diatomaceous earth and wash with ethanol until the filtrate is colorless. Concentrate the filtrate under reduced pressure to give dark oil. Subject residue to silica gel chromatography eluting with 1% then 2.5% MeOH/dichloromethane to afford the title compound (30.3 g, 98% yield) as an orange glass. (ES+): m/z 344 (M$^+$+H).

Preparation 23

[4-(4-Amino-isoquinolin-1-yloxy)-piperidin-1-yl]-(1-methyl-cyclopropyl)-methanone

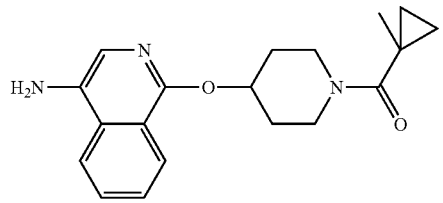

Add isoquinoline (500.00 g, 3.75 moles) and ethyl acetate (7.60 L, 77.62 moles) to a 22 L three-necked round-bottom flask in a water bath equipped with overhead stirrer, thermocoupler, nitrogen inlet/outlet, and addition funnel. Stir to dissolve. At room temperature add peracetic acid (1.25 L, 5.94 moles) dropwise over 0.5 ours. Stir at room temperature overnight. Chill the reaction flask in an ice-water bath, then quench the reaction by dropwise addition of dimethyl sulfide (525.00 mL, 7.14 moles) over 45 minutes. Stir overnight while warming to room temperature. Test the reaction mixture for peroxide.

Combine two lots of the reaction mixture. Transfer the reaction mixtures to a 50 L separatory funnel and add water (2.00 L, 111.02 moles) and dichloromethane (12.00 L, 187.21 moles). Add sodium carbonate (2.07 kg, 19.53 moles) in portions, then separate layers. Extract the aqueous layer with dichloromethane (3×4 L), combine the organic layers and dry over sodium sulfate. Filter and remove solvent under reduced pressure to afford a crude dark red oil/liquid.

Add ethyl acetate (8.00 L, 81.76 moles) to the crude dark red oil/liquid, then stir under reduced pressure until 6.8 L of ethyl acetate are removed. Filter the precipitated solid, wash with cold ethyl acetate (750.00 mL, 7.66 moles), then heptane (800.00 mL, 5.46 moles) wash. Dry the solid to afford isoquinoline-2-oxide, 714.20 g (64%) as a fine sand-like solid.

As an alternative work-up, prior to the heptane wash, remove 1 L of solvent from the filtrate. Allow the filtrate to stand overnight. Filter the solid and wash with cold ethyl acetate (500.00 mL, 5.11 moles), followed by a heptane (500.00 mL, 3.41 moles) wash. The solid was dried to afford isoquinoline-2-oxide, 110.10 g (10%) as a fine sand-like solid—crop#2 (total yield 74%).

Add isoquinoline 2-oxide (4.82 mol; 699.1 g), and acetic acid anhydride (73.95 mol; 6.99 L) to a 22 L flask with N$_2$ inlet, distillation head, and thermocouple. Heat the reaction mixture to a gentle reflux and removed volatile substances by distillation. Continue heating and collecting the distillate 2 hours (removing about half of the total reaction volume). Cool the reaction mixture to 50° C. Add methanol (2 L) drop wise, and allow reaction to warm to 70° C. Stir the reaction mixture overnight at room temperature. Isoquinolin-1-ol crystallizes from the solution, isolate by filtration and dry under reduced pressure at 50° C. Yield=246.7 grams (35%).

Add isoquinolin-1-ol (2.35 mol; 341.0 g), and 1705 mL 1:4 mixture of water and acetic acid to a 5 L flask. Heat the reaction mixture to 60° C. Add a solution of nitric acid (7.04 mol; 443.0 mL) in 1705 mL of a 1:4 mixture of water and acetic acid drop wise over 3 hours. Maintain a reaction temperature between 68-70° C. during the addition of nitric acid. After 3 hours, cool the reaction to room temperature. Add water (5564 mL) to the reaction mixture, then filter. Rinse the cake with water (1 L) and dry in vacuum at 50° C. Yield=196.8 grams (44%).

Add 1-hydroxy-4-nitroisoquinoline (880.3 mmol; 167.4 grams) and $POCl_3$ (4.95 mol; 460 mL) to a 2 L flask with $N_2$ inlet, condenser, and thermocouple. Heat the resulting slurry to 100° C. for approximately 1 hour. Concentrate the reaction mixture to dryness using a rotary evaporator. Slurry the residue in 1,2-dichloroethane (402 mL) and cool to 15° C. Add i-PrOH (1015 mL) drop wise while maintaining a pot temperature of less than 30° C. Stir the reaction mixture for 2 hours at 20° C. and 1 hour at 10° C. Filter the reaction mixture, and rinse the cake with isopropyl alcohol (100 mL). Dry under reduced pressure at 50° C. Yield=118.5 grams (65%).

Add 1-methyl-cyclopropanecarboxylic acid ethyl ester (405.0 g, 3.16 moles), 5 N sodium hydroxide (1.0 L, 5.00 moles), and methanol (400.0 mL, 9.88 moles) to a 3 L three-necked round-bottom flask. Heat the reaction mixture between 50° C. to 60° C. for 5 hours, then allow to cool to ambient temperature overnight. Remove the organic solvent and extract the basic solution with MTBE (2×500 mL). Adjust the pH of the aqueous solution to pH 1 using 600 mL conc. HCl and extract with MTBE (4×500 mL). Combine the organic layers, wash with saturate aq. sodium chloride, dry over magnesium sulfate, filter, and remove solvent under reduced pressure. Allow residue to solidify, then add 100 mL heptane and stir the resulting slurry at 0-5° C. Filter the slurry, then dry the resulting solid dried under reduced pressure. Concentrate the filtrate and cooled in an ice bath to afford additional white solid material. Combine to recover 265 g (84%) of 1-methyl-cyclopropanecarboxylic acid as a white solid.

Add 1-methyl-cyclopropanecarboxylic acid (260.0 g, 2.60 moles), 2-butanone (2.5 L, 27.92 moles), and N-methylmorpholine (325.0 mL, 2.95 moles) to a 5 L three-necked round-bottom flask equipped with overhead stirring. Stir the mixture at 0° C. and add 2-chloro-4,6-dimethoxy-[1,3,5]triazine (510.0 g, 2.86 moles) in portions over 30 minutes. Continue stirring at 0° C. for 15 minutes, then at ambient temperature for 2 hours. Filter the resulting N-methyl morpholine hydrochloride salt and rinse 2×200 mL 2-butanone. Concentrate the filtrate and dissolve the residue in 1500 mL THF to provide solution A.

Charge potassium carbonate (550.0 g, 3.94 moles) in 2 L water to a 5 L three-necked round-bottom flask. Add 4-hydroxypiperidine (275.0 g, 2.66 moles) to afford solution B.

Cool solution B in an ice-water bath and add solution A drop wise. Remove the cooling bath and stir the reaction mixture at room temperature for 2 hours. Remove the organic solvent under reduced pressure. Extract the remaining basic aqueous solution 6×2 L with dichloromethane. Combine the organics layers, wash with a mixture of 1.5 L saturated aq. sodium chloride and 200 mL conc. HCl. Extract the acidic aqueous solution with 3×1 L dichloromethane. Combine the organic layers and dry over 500 g magnesium sulfate and 100 g potassium carbonate overnight. Filter off the drying reagent and remove solvent until about 500 mL solvent remains. Add 1 L of heptane and remove solvent until crystallization occurs. Filter the solid, washing extensively with heptane, and dry under reduced pressure to afford (4-hydroxy-piperidin-1-yl)-(1-methyl-cyclopropyl)-methanone, 330 g (69%) as a white crystalline solid.

Add sodium hydride (38.40 g, 960.09 moles) and THF (1.54 L, 18.92 moles) to a 5 L Morton flask equipped with overhead stirrer, addition funnel, and thermocouple. Stir for several minutes, then add (4-hydroxy-piperidin-1-yl)-(1-methyl-cyclopropyl)-methanone (149.00 g, 813.09 moles). Stir for 0.5 hour. Add 1-chloro-4-nitro-isoquinoline (154.00 g, 738.24 moles) in THF (1.54 L, 18.92 moles) over 1 hour. Stir the reaction mixture for 2 hours at room temperature, then at 40° C. for 6 hours before cooling to room temperature overnight. Add water (500 mL, 27.78 moles) dropwise to the reaction mixture. Quench the reaction mixture by pouring into a vigorously stirring mixture of water (2.5 L, 138.89 moles) and MTBE (3.08 L, 25.92 moles). Separate the layers, wash the organic layer with water (3.08 L, 170.97 moles), and dry over sodium sulfate (142.00 g, 999.70 moles). Filter off the drying reagent to afford filtrate #1.

Repeat the above procedure to afford filtrate #2. Combine filtrate #1 and #2. Remove solvent under reduced pressure (~150 mm) and collect distillate with vapor temperature of 20-28° C. until about 1.5 L remains. Add isopropyl alcohol (4.62 L, 60.43 moles) to the distillation flask and resume distillation under reduced pressure (~120 mm), collecting distillate with vapor temperature of 35-44° C. until about 1 L remains. Chill the remaining slurry in ice overnight. Filter the solid and rinse with cold isopropyl alcohol (300.00 mL, 3.92 moles) followed by 3×100 mL heptane (300.00 mL, 2.05 moles). Dry the solid at 40° C. under reduced pressure overnight to afford (1-methyl-cyclopropyl)-[4-(4-nitro-isoquinolin-1-yloxy)-piperidin-1-yl]-methanone, 368 g (72%—combined) as an orange solid.

Charge a 3 gallon autoclave with (1-methyl-cyclopropyl)-[4-(4-nitro-isoquinolin-1-yloxy)-piperidin-1-yl]-methanone (368.0 g, 1.04 moles), THF (4.42 L, 54.32 moles), and 5% Pd on carbon (dry, 40.50 g, 19.03 moles). Seal the autoclave and introduce hydrogen to 50 psi. Stir the contents at 1000 rpm at room temperature under 50 psi of hydrogen for 4.5 hours. Filter and rinse with additional THF (2.0 L, 24.58 moles). Treat the filtrate with carbon (20-40 mesh, 42.00 g) and heat to 40° C. for 1 hour. Add additional carbon (60 mesh, 47.00 g) and continue heating for 1 hour. Filter carbon through a micro fiber paper and a bed of Hyflo Super Cel® and rinse with a minimal amount of THF. Remove solvent to obtain [4-(4-amino-isoquinolin-1-yloxy)-piperidin-1-yl]-(1-methyl-cyclopropyl)-methanone, 348 g (103%) as a dark orange-red oil/foam. $^1$H NMR (500 MHz, $CDCl_3$): δ 0.59 (t, J=6.0 Hz, 2H), 0.96 (t, J=6.0 Hz, 2H), 1.34 (s, 3H), 1.88-1.94 (m, 2H), 2.06-2.10 (m, 2H), 3.61-3.70 (m, 2H), 3.93-4.00 (m, 2H), 5.48-5.50 (m, 1H), 7.52 (s, 1H), 7.58 (t, J=7.0 Hz, 1H), 7.73 (t, J=7.0 Hz, 1H), 7.81 (d, J=7.0 Hz, 1H), 8.27 (d, J=8.5 Hz, 1H).

Preparation 24

[4-(4-amino-isoquinolin-1 yloxy)-piperidin-1-yl]-(2-fluoro-phenyl)methanone

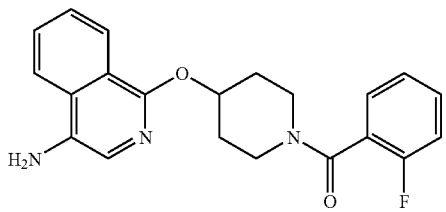

To a cold solution of 4-(4-nitro-isoquinoline-1-yloxy)-piperidine-1-carboxylic acid tert-butyl ester (9.68 g, 25.9 mmol, 0° C.) in DCM (100 mL) add TFA (80 mL). Stir at 22° C. for 2 hours, then remove solvent under reduced pressure.

Dissolve residue in DCM and treat with 1 N sodium hydroxide to pH~14. Isolate the aqueous phase and extract twice with DCM. Combine the organic phases and dry with anhydrous sodium sulfate. Removal of the solvent gives (4-nitro-isoquinoline-1-yloxy)-piperidine (7.06 g, 99% yield, ES+ (m/z) 274.3 [M+H]).

Stir a reaction mixture of 4-(4-nitro-isoquinoline-1-yloxy)-piperidine (4.0 g, 14.6 mmol), 2-fluorobenzoic acid (2.45 g, 17.5 mmol), DCC (3.6 g, 17.5 mmol), and HOBt (2.37 g, 17.5 mmol) in THF (100 mL) at 22° C. overnight. Filter then concentrate. Subject residue to silica gel chromatography eluting with hexanes and ethyl acetate to provide (2-fluoro-phenyl)-[4-(4-nitro-isoquinoline-1-yloxy)-piperidin-1-yl]-methanone as a yellow solid (6.82 g, 92% yield, ES+ (m/z) 396.3 [M+H]).

Stir a suspension of (2-fluoro-phenyl)-[4-(4-nitro-isoquinoline-1-yloxy)-piperidin-1-yl]-methanone (5.85 g, 14.8 mmol) and palladium on carbon (10%, 2.9 g) in methanol (250 mL) under hydrogen overnight. Remove the catalyst by filtration. Concentrate the filtrate to yield a pale yellow solid (4.7 g, 87% yield, ES+ (m/z) 366.3 [M+H]).

Prepare the following compound in a manner substantially analogous to the procedure set forth above.

| Preparation | Compound | Data MS (ES+): m/z [M + H] |
|---|---|---|
| Preparation 25 | [4-(4-Amino-isoquinolin-1-yloxy)-piperidin-1-yl]-(1-methyl-cyclopropyl)methanone | 326.3 |

Preparation 26

4-Nitro-1-piperazin-1-yl-isoquinoline

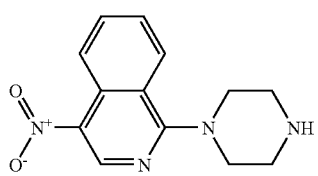

Treat a slurry of 1-chloro-4-nitro-isoquinoline (2.5 g, 12 mmol) in acetonitrile (100 mL) with solid piperazine (5.2 g, 60 mmol). Heat the resulting yellow mixture overnight at 60° C. After cooling to ambient temperature, partition the reaction mixture between ethyl acetate and a saturated aqueous sodium bicarbonate solution. Add MeOH, dichloromethane and ethyl acetate, and filter the entire mixture to give a bright yellow solid. (2.15 g, 69%; LCMS ES+ (m/z) 259 [M+H]).

Preparation 27

Cyclopropyl-[4-(4-nitro-isoquinolin-1-yl)-piperazin-1-yl]-methanone

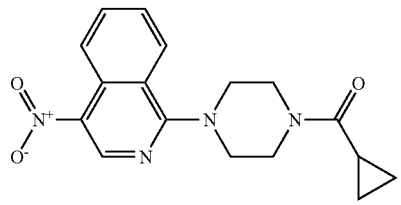

Treat a solution or slurry of 4-nitro-1-piperazin-1-yl-isoquinoline (Preparation 26, 517 mg, 2 mmol), cyclopropanecarboxylic acid (258 mg, 3 mmol) and catalytic DMAP (24 mg, 0.2 mmol) in dichloromethane (20 mL) with EDCI (575 mg, 3 mmol). Agitate the resulting mixture at ambient temperature overnight, then wash with saturated aqueous sodium bicarbonate solution. Dry the organic layer over sodium sulfate and concentrate under reduced pressure. Subject residue to silica gel chromatography using a gradient of 0-2% 2M ammonia-methanol in dichloromethane and a gradient of 0-70% ethyl acetate in hexanes to give a yellow solid after two purifications. (513 mg, 79% yield, LCMS ES+ (m/z) 327 [M+H]).

Prepare the following compounds in a manner substantially analogous to the procedure set forth above.

| Preparation | Compound | Data MS (ES+): m/z |
|---|---|---|
| Preparation 28 | (1-Methyl-cyclopropyl)-[4-(4-nitro-isoquinolin-1-yl)-piperazin-1-yl]-methanone 76% yield | 341 [M + H] |
| Preparation 29 | (2,6-Difluoro-phenyl)-[4-(4-nitro-isoquinolin-1-yl)-piperazin-1-yl]-methanone 50% yield | 399.1 [M + H] |
| Preparation 30 | 2,2-Dimethyl-1-[4-(4-nitro-isoquinolin-1-yl)-piperazin-1-yl]-propan-1-one. 66% yield | 343.2 [M + H] |

Preparation 3

1[4-(4-Amino-isoquinolin-1-yl)-piperazin-1-yl]-cyclopropyl-methanone

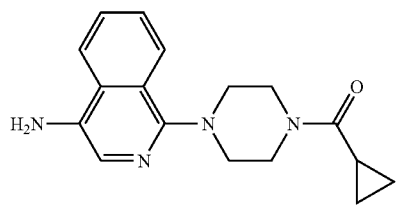

Subject a slurry of cyclopropyl-[4-(4-nitro-isoquinolin-1-yl)-piperazin-1-yl]-methanone (Preparation 27; 513 mg, 1.57 mmol) and 5% palladium on carbon (91 mg) in ethyl acetate (50 mL) in a Parr shaker at ambient temperature to an atmosphere of hydrogen at 60 psi. After 8 h, filter the reaction mixture and concentrate under reduced pressure to give a brown foam. (Quantitative yield; LCMS ES+(m/z) 297 [M+H]).

Prepare the following compounds in a manner substantially analogous to the procedure described above.

| Preparation | Compound | Data MS (ES+): m/z |
|---|---|---|
| Preparation 32 | 1-[4-(4-Amino-isoquinolin-1-yl)-piperazin-1-yl]-2,2-dimethyl-propan-1-one. (rxn time 24 hours) | 313 [M + H] |
| Preparation 33 | [4-(4-Amino-isoquinolin-1-yl)-piperazin-1-yl]-(2,6-difluoro-phenyl)-methanone. (rxn time 24 hours) | 369 [M + H] |
| Preparation 34 | [4-(4-Amino-isoquinolin-1-yl)-piperazin-1-yl]-(1-methyl-cyclopropyl)-methanone. | 311 [M + H] |

Preparation 35

[4-(4-Amino-isoquinolin-1-yl)-piperazin-1-yl]-(2-fluoro-phenyl)-methanone

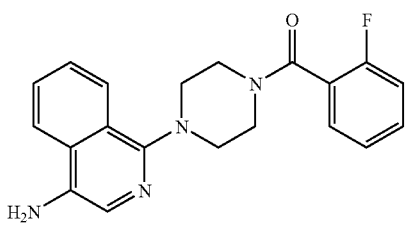

To a solution of piperazine-1-carboxylic acid tert-butyl ester (10 g, 53.7 mmol) in dichloromethane (300 mL), add triethyl amine (15.1 mL, 107.4 mmol) and 2-fluorobenzoyl chloride (6.4 mL, 53.7 mmol). Stir the mixture at room temperature overnight. Then add water (200 mL) and separate the organic layer, dry over sodium sulfate, filter and evaporate solvent under reduced pressure to give 17.3 g of 4-(2-fluoro-benzoyl)-piperazine-1-carboxylic acid tert-butyl ester. ES+ (m/z) 309[M+H].

To a solution of 4-(2-fluoro-benzoyl)-piperazine-1-carboxylic acid tert-butyl ester (16.3 g, 53 mmol) in dichloromethane (100 mL), add a solution of 4 M HCl in 1,4-dioxane (40 mL, 159 mmol) and stir the reaction mixture at room temperature overnight. Add Et$_2$O to the resultant white suspension and evaporate solvents under reduced pressure to give 12.6 g of (2-fluoro-phenyl)-piperazin-1-yl-methanone hydrochloride. ES+ (m/z) 209[M+H]).

Add (2-fluoro-phenyl)-piperazin-1-yl-methanone (3.16 g, 12.9 mmol) and K$_2$CO$_3$ (8.9 g, 64.5 mmol) to 1-chloro-4-nitroisoquinoline (2.85 g, 13.7 mmol) in acetonitrile (100 mL) and stir for 24 hours. Filter the insoluble solid and wash the cake with AcOEt. Evaporate the solvent under reduced pressure to give a residue. Subject residue to silica gel chromatography eluting with hexane:AcOEt 20-90% to give 3.72 g of (2-fluoro-phenyl)-[4-(4-nitro-isoquinolin-1-yl)-piperazin-1-yl]-methanone as a solid. LCMS ES+(m/z) 381.2 [M+H].

Add Na$_2$S$_2$O$_4$ (60.87 g, 39.4 mmol) followed by NH$_4$OH 32% (15 mL) to (2-fluoro-phenyl)-[4-(4-nitro-isoquinolin-1-yl)-piperazin-1-yl]-methanone (3 g, 7.89 mmol) in 170 mL of 1:1 mixture of THF:H$_2$O and stir for 90 min. Dilute with water and extract with AcOEt several times. Combine organics and wash with saturated aq. sodium chloride, dry over Na$_2$SO$_4$ and evaporate under reduced pressure to give 1.8 g of the title compound as a solid. LCMS ES+ (m/z) 351.2 [M+H].

Preparation 36

1-[5-(1-Methyl-cyclopropyl)-2-p-tolyl-2H-pyrazol-3-yl]-3-[1-(piperidin-4-yloxy)-isoquinolin-4-yl]-urea dihydrochloride

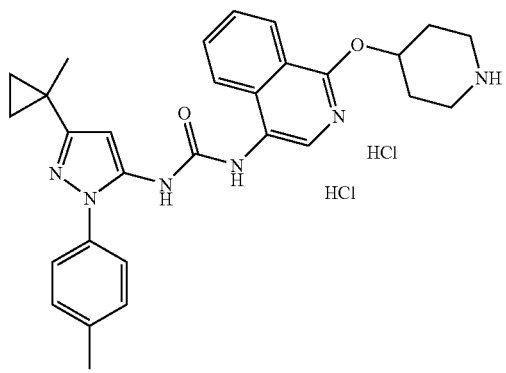

Dissolve [5-(1-methyl-cyclopropyl)-2-p-tolyl-2H-pyrazol-3-yl]-carbamic acid 2,2,2-trichloro-ethyl ester (Preparation 18, 3.20 g, 7.94 mmol and 2.0 equiv) and 4-(4-amino-isoquinolin-1-yloxy)-piperidine-1-carboxylic acid tert-butyl ester (Preparation 22, 1.37 g, 3.97 mmol, 1.0 equiv) in 7 mL of anhydrous DMSO, add diisopropylethyl amine (DIPEA, 1.36 mL, 7.94 mmol, 2.0 equiv) and heat in a sealed tube with stirring for 20 hours at 80° C. Pour the solution in a 1:1 v/v mixture of dichloromethane and iced water. Extract the aqueous phase with dichloromethane (2×50 mL), and wash the combined organic layers with water (2×50 mL) and aqueous sodium chloride (100 mL). Dry the organic solution over sodium sulfate and evaporate under reduced pressure. Subject residue to silica gel chromatography eluting with a gradient from 15% to 80% EtOAc in hexanes to afford 1.40 g of 4-(4-{3-[5-(1-methyl-cyclopropyl)-2-p-tolyl-2H-pyrazol-3-yl]-ureido}-isoquinolin-1-yloxy)-piperidine-1-carboxylic acid tert-butyl ester as a pure foamy cream solid. 59% yield. ES+ (m/z) 597.4 [M+H].

Add HCl 4 M in dioxane (2.4 mL, 9.36 mmol) to 4-(4-{3-[5-(1-methyl-cyclopropyl)-2-p-tolyl-2H-pyrazol-3-yl]-ureido}-isoquinolin-1-yloxy)-piperidine-1-carboxylic acid tert-butyl ester (1.4 g, 2.34 mmol) in dichloromethane (20 mL) at room temperature and stir overnight. Evaporate the solvent under reduced pressure to give the title compound (1.3 g) as a white solid (quantitative). ES+ (m/z): 497.4 (M+H).

Preparation 37

1-[5-(2-Fluoro-1-fluoromethyl-1-methyl-ethyl)-2-p-tolyl-2H-pyrazol-3-yl]-3-[1-(piperidin-4-yloxy)-isoquinolin-4-yl]-urea hydrochloride Add [5-(2-fluoro-1-fluoromethyl-1-methyl-ethyl)-2-p-tolyl-2H-pyrazol-3-yl]-carbamic acid 2,2,2-trichloro-ethyl ester (Preparation 27, 2.7 mmol, 1.2 g) and DIPEA (2.9 mmol, 0.5 mL) to a solution of 4-(4-amino-isoquinolin-1- yloxy)-piperidine-1-carboxylic acid tert-butyl ester (Preparation 22, 2.9 mmol, 1.0 g) in 4 mL of DMSO and stir at 85° C. overnight. Cool down, add water and extract with dichloromethane. Combine the organic layers and wash with saturated aq. sodium chloride. Dry over sodium sulfate, filter, and concentrate under reduced pressure to give a residue. Subject residue to silica gel chromatography eluting with hexanes/ethyl acetate in gradient (from 15 to 70%) to yield 4-(4-{3-[5-(2-fluoro-1-fluoromethyl-1-methyl-ethyl)-2-p-tolyl-2H-pyrazol-3-yl]-ureido}-isoquinolin-1-yloxy)-piperidine-1-carboxylic acid tert-butyl ester. LCMS ES+ (m/z) 635 [M+H].

Stir 4-(4-{3-[5-(2-fluoro-1-fluoromethyl-1-methyl-ethyl)-2-p-tolyl-2H-pyrazol-3-yl]-ureido}-isoquinolin-1-yloxy)-piperidine-1-carboxylic acid tert-butyl ester (1.1 mmol, 0.6 g) and dissolve in 5 mL of dichloromethane and hydrogen chloride 4.0 M in dioxane (5.3 mmol, 1.3 mL) at room temperature overnight. Concentrate under reduced pressure. Triturate the white solid formed with diethyl ether. LCMS ES+ (m/z) 535 [M+H].

Prepare the following compounds in a manner substantially analogous to the procedures described above.

| Preparation | Compound | Data MS (ES+): m/z [M + H] |
|---|---|---|
| Preparation 38 | 1-[5-(1,1-Bis-fluoromethyl-propyl)-2-p-tolyl-2H-pyrazol-3-yl]-3-[1-(piperidin-4-yloxy)-isoquinolin-4-yl]-urea hydrochloride | 549 |
| Preparation 39 | 1-[5-(2-Fluoro-1,1-dimethyl-ethyl)-2-p-tolyl-2H-pyrazol-3-yl]-3-[1-(piperidin-4-yloxy)-isoquinolin-4-yl]-urea hydrochloride | 517 |

Preparation 40

1-(5-tert-Butyl-2-p-tolyl-2H-pyrazol-3yl)-3-[1(piperidin-4-yloxy)-isoquinolin-4-yl]-urea

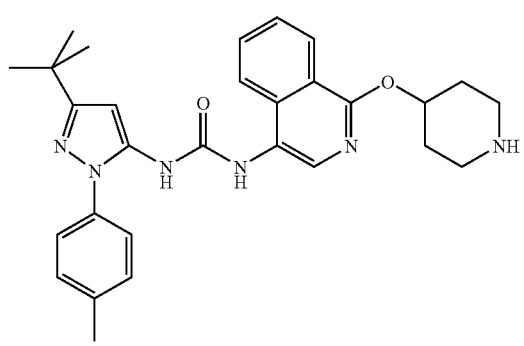

Bubble nitrogen gas through a solution of 1-(5-tert-butyl-2-p-tolyl-2H-pyrazol-3-yl)-carbamic acid 2,2,2-trichloroethyl ester (Preparation 17, 589 mg, 1.456 mmol) and 4-(4-amino-isoquinolin-1-yloxy)-piperidine-1-carboxylic acid tert-butyl ester (Preparation 22, 500 mg, 1.456 mmol) in DMSO (5 mL) for 5 min. Next add N,N-diisopropylethylamine (507 μL, 2.912 mmol). Stir at 60° C. for 6 hours then allowed to cool to room temperature over overnight. Partition the reaction mixture between 200 mL of CH₂Cl₂ and 100 mL distilled water. Wash with water (1×100 mL), then combine the aqueous layers and extract with CH₂Cl₂ (3×50 mL). Combine organic layers and wash with saturated aq. sodium chloride (2×100 mL). Dry the combined organic phases over sodium sulfate and concentrate. Subject residue to silica gel chromatography eluting with hexanes and ethyl acetate to give 4-{4-[3-(5-tert-butyl-2-p-tolyl-2H-pyrazol-3-yl)-ureido]-isoquinolin-1-yloxy}-piperidine-1-carboxylic acid tert-butyl ester as a brown solid. LCMS ES+ (m/z) 599.5 [M+H]

To a cold solution of 4-{4-[3-(5-tert-butyl-2-p-tolyl-2H-pyrazol-3-yl)-ureido]-isoquinolin-1-yloxy}-piperidine-1-carboxylic acid tert-butyl ester (820 mg, 1.37 mmol) in dichloromethane (50 mL), add trifluoroacetic acid (15 mL). Stir the reaction mixture at 22° C. for 1.5 hours. After removal of solvent, treat the residue with 1N sodium hydroxide saturated with NaCl (50 mL) and extract five times with dichloromethane (50 mL each). Dry the combined organic phases over sodium sulfate. Filter the mixture and subject residue to silica gel chromatography eluting with dichloromethane and methanol to provide a white solid (515 mg, 75% yield, LCMS ES+ (m/z) 499.5 [M+H]).

Prepare the following compounds in a manner substantially analogous to the procedures set forth above.

TABLE 3

| Preparation | Compound | Data MS (ES+): m/z |
|---|---|---|
| Preparation 41 | 1-(5-Pentafluoroethyl-2-p-tolyl-2H-pyrazol-3-yl)-3-[1-(piperidin-4-yloxy)-isoquinolin-4-yl]-urea | 561.3 [M + H] |
| Preparation 42 | 1-[1-(Piperidin-4-yloxy)-isoquinolin-4-yl]-3-2-p-tolyl-5-(1-trifluoromethyl-cyclopropyl)-2H-pyrazol-3-yl]-urea | 551.4 [M + H] |

EXAMPLE 1

1-[1-(4-Cyclopropanecarbonyl-piperazin-1-yl)-isoquinolin-4-yl]-3-[5-(1-methyl-cyclopropyl)-2-p-tolyl-2H-pyrazol-3-yl]-urea

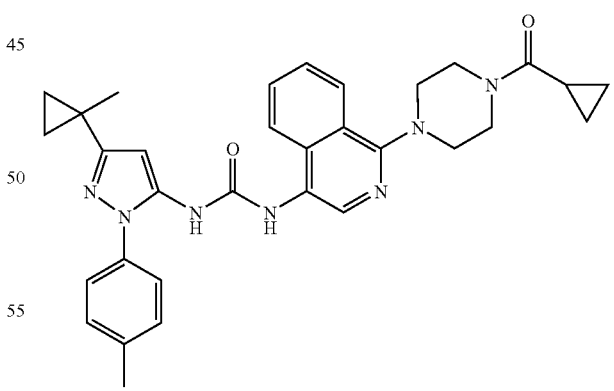

Heat a solution of [4-(4-amino-isoquinolin-1-yl)-piperazin-1-yl]-cyclopropyl-methanone (Preparation 29, 214 mg, 0.722 mmol), [5-(1-methyl-cyclopropyl)-2-p-tolyl-2H-pyrazol-3-yl]-carbamic acid 2,2,2-trichloro-ethyl ester (Preparation 18, 290 mg, 0.722 mmol) and diisopropylethylamine (0.264 mL) in 4 mL of DMSO at 60° C. for 5 hours. Cool the resulting mixture to ambient temperature, and add water. Filter the precipitate, rinse with water, then pentane, and vacuum oven dry at 60° C. Subject residue to silica gel chromatography eluting with a gradient of 2M ammonia-methanol in dichloromethane (0 to 2%) to give 206 mg of product (93% purity by LCMS).

Dissolve in a small amount of dichloromethane and MeOH, treat with 1 equivalent of 2 M methanesulfonic acid in dichloromethane and concentrate under a stream of nitrogen. Triturate the resulting solid with a few mLs of DMSO/MeOH/water and filter to give 145 mg of the free base (LCMS ES+ (m/z) 550 [M+H]).

Prepare the following compound, after further purification by reverse phase on an Xterra 30×75 mm 5 micron MS C18 column using a gradient of aqueous 10 mM ammonium bicarbonate in acetonitrile, in a manner substantially analogous to the procedure described above.

| EXAMPLE | Compound | Data MS (ES+): m/z [M + H] |
|---|---|---|
| Example 2 | 1-{1-[4-(1-Methyl-cyclopropanecarbonyl)-piperazin-1-yl]-isoquinolin-4-yl}-3-[5-(1-methyl-cyclopropyl)-2-p-tolyl-2H-pyrazol-3-yl]-urea | 564 |

EXAMPLE 3

1-{1-[4-(2,6-Difluoro-benzoyl)-piperazin-1-yl]-isoquinolin-4-yl}-3-[5-(1-methyl-cyclopropyl)-2-p-tolyl-2H-pyrazol-3-yl]-urea Heat a solution of [4-(4-amino-isoquinolin-1-yl)-piperazin-1-yl]-(2,6-difluoro-phenyl)-methanone (Preparation 32, approx. 0.88 mmol), [5-(1-methyl-cyclopropyl)-2-p-tolyl-2H-pyrazol-3-yl]-carbamic acid 2,2,2-trichloro-ethyl ester (Preparation 18, 362 mg, 0.9 mmol) and diisopropylethylamine (0.314 mL) in 5 mL of DMSO at 60° C. overnight. Cool the resulting mixture to ambient temperature and partition between water and ethyl acetate using saturated aq. sodium chloride to aid phase separation. Extract the aqueous layer with ethyl acetate, and dry the combined organic layer over sodium sulfate. Concentrate under reduced pressure. Subject residue to silica gel chromatography eluting with a gradient of 2 M ammonia-methanol in dichloromethane (0 to 2%). Dissolve in a small amount of dichloromethane and MeOH, treat with 1 equivalent of 2 M methanesulfonic acid in dichloromethane and concentrate under a stream of nitrogen. Further purification by reverse phase on an Xterra 30×75 mm 5 micron MS C18 column using a gradient of aqueous 10 mM ammonium bicarbonate in acetonitrile gives 73 mg of the free base. LCMS ES+ (m/z) 622 [M+H]).

Prepare the freebase of the following compound utilizing a procedure substantially analogous to that described above Then dissolve 0.13 g in 1 mL of DCM and add a solution of methanesulfonic acid 1 N in DCM (1 eq.). Evaporate solvent under reduced pressure give 0.15 g of the compound described below.

| EXAMPLE | Compound | Data MS (ES+): m/z [M + H] |
|---|---|---|
| Example 4 | 1-{1-[4-(2-Fluoro-benzoyl)-piperazin-1-yl]-isoquinolin-4-yl}-3-[5-(1-methyl-cyclopropyl)-2-p-tolyl-2H-pyrazol-3-yl]-urea mesylate | 604 |

EXAMPLE 5

1-(5-tert-Butyl-2-p-tolyl-2H-pyrazol-3-yl)-3-{1-[1-(1-methyl-cyclopropanecarbonyl)-piperidin-4-yloxy]-isoquinolin-4-yl}-urea Bubble nitrogen gas through a solution of 1-(5-tert-butyl-2-p-tolyl-2H-pyrazol-3-yl)-carbamic acid 2,2,2-trichloro-ethyl ester (Preparation 17, 203 mg, 0.5 mmol) and [4-(4-amino-isoquinolin-1-yloxy)-piperidin-1-yl]-(1-methyl-cyclopropyl)methanone (163 mg, 0.5 mmol) in DMSO (2 mL) for 5 min. Next, add N,N-diisopropylethylamine (200 μL, 1.1 mmol). After stirring at 60° C. overnight, partition the reaction mixture between dichloromethane (15 mL) and saturated sodium bicarbonate (50 mL). Isolate the aqueous phase and extract twice with dichloromethane (15 mL each). Dry the combined organic phases over sodium sulfate and concentrate. The residue is purified on a silica gel chromatography with hexanes and ethyl acetate to give a white solid (226 mg, 78% yield, ES+ (m/z) 581.3 [M+H]).

Prepare the free base of the following compounds in a manner substantially analogous to the procedure described above. Then dissolve in 1 mL of DCM and add a solution of methanesulfonic acid 1 N in DCM (1 eq.). Evaporate solvent under reduced pressure give the compound described below.

| EXAMPLE | Compound | MS (ES+): m/z [M + H] |
|---|---|---|
| Example 6 | 1-{1-[4-(2,2-Dimethyl-propionyl)-piperazin-1-yl]-isoquinolin-4-yl}-3-[5-(1-methyl-cyclopropyl)-2-p-tolyl-2H-pyrazol-3-yl]-urea mesylate | 566 |
| Example 7 | 1-[5-tert-Butyl-2-(6-methyl-pyridin-3-yl)-2H-pyrazol-3-yl]-{1-[1-(1-methyl-cyclopropanecarbonyl)-piperidin-4-yloxy]-isoquinolin-4-yl}-urea mesylate | 582.3 |
| Example 8 | 1-{1-[1-(2-Fluoro-benzoyl)-piperidin-4-yloxy]-isoquinolin-4-yl}-3-[5-(1-methoxy-cyclopropyl)-2-p-tolyl-2H-pyrazol-3-yl]-urea mesylate | 635.0 |
| Example 9 | 1-[5-(1-Methoxy-cyclopropyl)-2-p-tolyl-2H-pyrazol-3-yl]-3-{1-[1-(1-methyl-cyclopropanecarbonyl)-piperidin-4-yloxy]-isoquinolin-4-yl}-urea mesylate | 595.3 |
| Example 10 | 1-[2-(6-Methyl-pyridin-3-yl)-5-(1-trifluoromethyl-cyclopropyl)-2H-pyrazol-3-yl]-3-{1-[1-(3-methyl-thiophene-2-carbonyl)-piperidin-4-yloxy]-isoquinolin-4-yl}-urea mesylate | 634.0 |

EXAMPLE 11

1-(5-tert-Butyl-2-p-tolyl-2H-pyrazol-3-yl)-3-{1-[4-(2,2-dimethyl-propionyl)-piperazin-1-yl]-isoquinolin-4yl}-urea mesylate Stir 1-[4-(4-Amino-isoquinolin-1-yl)-piperazin-1-yl]-2,2-dimethyl-propan-1-one (Preparation 3, 0.9 mmol, 0.3 g) dissolved in 18 mL of acetonitrile. Add potassium carbonate (0.99 mmol, 0.1 g) and 1-(5-tert-butyl-2-p-tolyl-2H-pyrazol-3-yl)-carbamic acid 2,2,2-trichloro-ethyl ester (Preparation 17, 0.9 mmol, 0.4 g) and stir overnight at room temperature. Then add 1 mL of DMF and stir at 60° C. for 24 hours. Cool down, add water and extract with dichloromethane. Combine the organic layers and wash with saturated aq. sodium chloride, dry over sodium sulfate, filter, and concentrate under reduced pressure to give a residue. Subject residue to silica gel chromatography eluting with hexanes/ethyl acetate in gradient (from 5% to 20%). Add dichloromethane over the oil obtained and filter the precipitate formed to obtain 1-(5-tert-butyl-2-p-tolyl-2H-pyrazol-3-yl)-3-{1-[4-(2,2-dimethyl-propionyl)-piperazin-1-yl]-isoquinolin-4-yl}-urea. ES+ (m/z) 568[M+H]).

Stir 1-(5-tert-butyl-2-p-tolyl-2H-pyrazol-3-yl)-3-{1-[4-(2,2-dimethyl-propionyl)-piperazin-1-yl]-isoquinolin-4-yl}-urea at room temperature. Add 1N methanesulfonic acid solution in dichloromethane to form the title compound. LCMS ES+ (m/z) 568 [M+H].

EXAMPLE 12

1-{1-[1-(1-Methyl-cyclopropanecarbonyl)-piperidin-4-yloxy]-isoquinolin-4-yl}-3-[5-(1-methyl-cyclopropyl)-2-p-tolyl-2H-pyrazol-3-yl]-urea mesylate

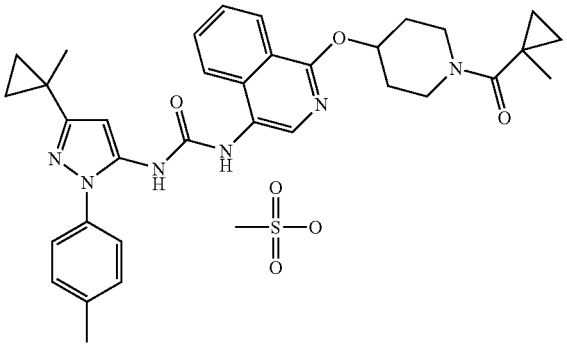

Place EDCI (0.147 g, 0.77 mmol), HOBt (0.10 g, 0.77 mmol), 1-[5-(1-methyl-cyclopropyl)-2-p-tolyl-2H-pyrazol-3-yl]-3-[1-(piperidin-4-yloxy)-isoquinolin-4-yl]-urea dihydrochloride (Preparation 3, 0.16 g, 0.64 mmol) and 1-methyl-1-cyclopropyl carboxylic acid (1.1 eq) in a flask under $N_2$. Add dichloromethane (5 mL) follow by DIPEA (0.22 mL, 1.28 mmol) and stir at room temperature overnight. Evaporate solvent to give a residue. Subject residue to silica gel chromatography eluting with hexane:AcOEt 50-100% to give 1-{1-[1-(1-methyl-cyclopropanecarbonyl)-piperidin-4-yloxy]-isoquinolin-4-yl}-3-[5-(1-methyl-cyclopropyl)-2-p-tolyl-2H-pyrazol-3-yl]-urea as a free base. ES+ (m/z) 579.3 (M+H).

Dissolve 0.3 g of 1-{1-[1-(1-Methyl-cyclopropanecarbonyl)-piperidin-4-yloxy] isoquinolin-4-yl}-3-[5-(1-methyl-cyclopropyl)-2-p-tolyl-2H-pyrazol-3-yl]-urea in dichloromethane 1 mL and add 321 μL of a solution of methanesulfonic acid 1 N in dichloromethane. Evaporation of solvent under reduced pressure gives 0.357 g of the title compound as a white solid (quantitative). ES+ (m/z) 579.3 (M+H).

Prepare the following compounds in a manner substantially analogous to the preparations described above.

| EXAMPLE | Compound | Data MS (ES+): m/z [M + H] |
|---|---|---|
| Example 13 | 1-{1-[1-(2-Fluoro-benzoyl)-piperidin-4-yloxy]-isoquinolin-4-yl}-3-[5-(1-methyl-cyclopropyl)-2-p-tolyl-2H-pyrazol-3-yl]-urea mesylate | 619.3 |
| Example 14 | 1-[1-(1-Cyclopropanecarbonyl-piperidin-4-yloxy-isoquinolin-4-yl]-3-[5-(1-methyl-cyclopropyl)-2-p-tolyl-2H-pyrazol-3-yl]-urea mesylate | 565.3 |
| Example 15 | 1-{1-[1-(2,6-Difluoro-benzoyl)-piperidin-4-yloxy]-isoquinolin-4-yl}-3-[5-(1-methyl-cyclopropyl)-2-p-tolyl-2H-pyrazol-3-yl]-urea mesylate | 637.3 |

-continued

| EXAMPLE | Compound | Data MS (ES+): m/z [M + H] |
|---|---|---|
| Example 16 | 1-{1-[1-(2-Methyl-benzoyl)-piperidin-4-yloxy]-isoquinolin-4-yl}-3-[5-(1-methyl-cyclopropyl)-2-p-tolyl-2H-pyrazol-3-yl]-urea mesylate | 615.4 |
| Example 17 | 1-{1-[1-(2-Chloro-6-fluoro-benzoyl)-piperidin-4-yloxy]-isoquinolin-4-yl}-3-[5-(1-methyl-cyclopropyl)-2-p-tolyl-2H-pyrazol-3-yl]-urea mesylate | 653.3 |
| Example 18 | 1-{1-[1-(2-Methoxy-benzoyl)-piperidin-4-yloxy]-isoquinolin-4-yl}-3-[5-(1-methyl-cyclopropyl)-2-p-tolyl-2H-pyrazol-3-yl]-urea mesylate | 631.3 |
| Example 19 | 1-[5-(1-Methyl-cyclopropyl)-2-p-tolyl-2H-pyrazol-3-yl]-3-{1-[1-(1-trifluoromethyl-cyclopropanecarbonyl)-piperidin-4-yloxy]-isoquinolin-4-yl}-urea mesylate | 634.3 |
| Example 20 | 1-{1-[1-(3-Fluoro-2-fluoromethyl-2-methyl-propionyl)-piperidin-4-yloxy[-isoquinolin-4-yl}-3-[5-(1-methyl-cyclopropyl)-2-p-tolyl-2H-pyrazol-3-yl]-urea mesylate | 618.4 |
| Example 21 | 1-[5-(2-Fluoro-1-fluoromethyl-1-methyl-ethyl)-2-p-tolyl-2H-pyrazol-3-yl]-3-{1-[1-(1-methyl-cyclopropanecarbonyl)-piperidin-4-yloxy]-isoquinolin-4-yl}-urea mesylate | 617 |
| Example 22 | 1-[5-(2-Fluoro-1,1-dimethyl-ethyl)-2-p-tolyl-2H-pyrazol-3-yl]-3-{1-[1-(1-methyl-cyclopropanecarbonyl)-piperidin-4-yloxy]-isoquinolin-4-yl}-urea mesylate | 599 |

EXAMPLE 23

4-{4-[3-(5-tert-butyl-2-p-tolyl-2H-pyrazol-3-yl)-ureido]-isoquinolin-1-yloxy}-piperazine-1-carboxylic acid amide

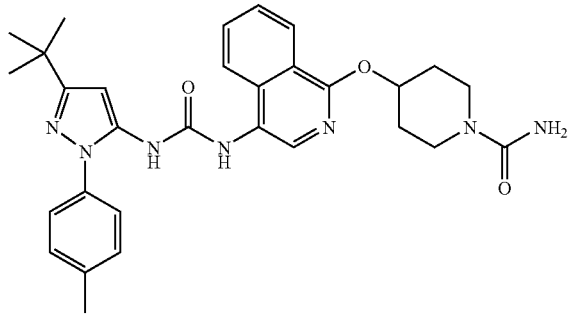

Bubble nitrogen gas through a solution of 1-(5-tert-butyl-2-p-tolyl-2H-pyrazol-3-yl)-3-[1(piperidin-4-yloxy)-isoquinolin-4-yl]-urea (Preparation 39, 100 mg, 0.2 mmol) and carbamic acid phenyl ester (32.9 mg, 0.24 mmol) in DMSO (1 mL) for 5 min. Next, add N,N-diisopropylethylamine (200 µL, 1.1 mmol). After stirring at 85° C. overnight, partition the reaction mixture between ethyl acetate (15 mL) and saturated sodium bicarbonate (50 mL). Isolate the aqueous phase and extract twice with ethyl acetate (15 mL each). Dry the combined organic phases over sodium sulfate and concentrate. Subject residue to silica gel chromatography eluting with hexanes and ethyl acetate to give a white solid (40 mg, 37% yield, ES+ (m/z) 542.3 [M+H]).

EXAMPLE 24

1-(5-tert-Butyl-2-p-tolyl-2H-pyrazol-3-yl)-3-{1-[1-(2-fluoro-benzol)-piperidin-4-yloxy]-isoquinolin-4-yl}-urea mesylate Stir a reaction mixture of 1-(5-tert-butyl-2-p-tolyl-2H-pyrazol-3-yl)-3-[1 (piperidin-4-yloxy)-isoquinolin-4-yl]-urea (Preparation 39, 110 mg, 0.221 mmol), 2-fluorobenzoic acid (37.1 mg, 0.265 mmol), HOBt (35.8 mg, 0.265 mmol), and DCC (54.6 mg, 0.265 mmol) in THF (3 mL) at 22° C. for 18 h. Filter the mixture and pour filtrate into separatory funnel containing CH$_2$Cl$_2$ (100 mL). Wash with 1N NaOH (2×20 mL), combine aqueous layers and extract with CH$_2$Cl$_2$ (2×50 mL), then wash combined organic layer with saturated aq. sodium chloride (1×50 mL). Dry the combined organic phases over sodium sulfate, filter the mixture and subject residue to silica gel chromatography eluting with dichloromethane and methanol to provide a white solid (109.8 mg, 80% yield, ES+ (m/z) 621.5 [M+H]).

Dissolve 0.107 g of 1-(5-tert-Butyl-2-p-tolyl-2H-pyrazol-3-yl)-3-{3-chloro-1-(2-fluoro-benzoyl)-piperidin-4-yloxy]-isoquinolin-4-yl)}-urea in dichloromethane (2 mL) and methanol (2 mL) and add methane sulfonic acid (16.56 mg, 0.1723 mmol). Evaporation of solvent under reduced pressure give the title compound as a white solid (119.7 mg, 97%, ES+ (m/z) 621.5 [M+H–MsOH].

Prepare the following compounds in a manner substantially analogous to the procedure described above.

| EXAMPLE | Compound | Data MS (ES+): m/z [M + H] |
|---|---|---|
| Example 25 | 1-[5-tert-Butyl-2-(6-methyl-pyridin-3-yl)-2H-pyrazol-3-yl]-3-{1-[1-(3-methyl-thiophene-2-carbonyl)-piperidin-4-yloxy]-isoquinolin-4-yl}-urea mesylate | 624.0 |
| Example 26 | 1-[5-tert-Butyl-2-(6-methyl-pyridin-3-yl)-2H-pyrazol-3-yl]-3-{1-[1-(2-chloro-benzoyl)-piperidin-4-yloxy]-isoquinolin-4-yl}-urea mesylate | 638.0 |
| Example 27 | 1-[5-tert-Butyl-2-(6-methyl-pyridin-3-yl)-2H-pyrazol-3-yl]-3-{1-[1-(2-fluoro-benzoyl)-piperidin-4-yloxy]-isoquinolin-4-yl}-urea mesylate | 622.3 |
| Example 28 | 1-[5-tert-Butyl-2-(6-methyl-pyridin-3-yl)-2H-pyrazol-3-yl]-3-{1-[1-(2,6-difluoro-benzoyl)-piperidin-4-yloxy]-isoquinolin-4-yl}-urea mesylate | 640.3 |
| Example 29 | 1-[2-(6-Methyl-pyridin-3-yl)-5-(1-trifluoromethyl-cyclopropyl)-2H-pyrazol-3-yl]-3-{1-[1-(3-methyl-thiophene-2-carbonyl)-piperidin-4-yloxy]-isoquinolin-4-yl}-urea mesylate | 676.0 |
| Example 30 | 1-{1-[1-(2-Chloro-benzoyl)-piperidin-4-yloxy]-isoquinolin-4-yl}-3-[2-(6-methyl-pyridin-3-yl)-5-(1-trifluoromethyl-cyclopropyl)-2H-pyrazol-3-yl]-urea mesylate | 690.0 |
| Example 31 | 1-{1-[1-(2-Fluoro-benzoyl)-piperidin-4-yloxy]-isoquinolin-4-yl}-3-[2-(6-methyl-pyridin-3-yl)-5-(1-trifluoromethyl-cyclopropyl)-2H-pyrazol-3-yl]-urea mesylate | 674.0 |
| Example 32 | 1-{1-[1-(2,6-Difluoro-benzoyl)-piperidin-4-yloxy]-isoquinolin-4-yl}-3-[2-(6-methyl-pyridin-3-yl)-5-(1-trifluoromethyl-cyclopropyl)-2H-pyrazol-3-yl]-urea mesylate | 692.0 |
| Example 33 | 1-(5-tert-Butyl-2-p-tolyl-2H-pyrazol-3-yl)-3-{1-[1-(3-methyl-thiophene-2-carbonyl)-piperidin-4-yloxy]-isoquinolin-4-yl}-urea mesylate | 623.5 |
| Example 34 | 1-(5-tert-Butyl-2-p-tolyl-2H-pyrazol-3-yl)-3-[1-(1-cyclopropanecarbonyl-piperidin-4-yloxy)-isoquinolin-4-yl]-urea mesylate | 567.5 |
| Example 35 | 1-{1-[1-(2-Fluoro-benzoyl)-piperidin-4-yloxy]-isoquinolin-4-yl}-3-(5-pentafluoroethyl-2-p-tolyl-2H-pyrazol-3-yl)-urea mesylate | 683.0 |
| Example 36 | 1-{1-[1-(1-Methyl-cyclopropanecarbonyl)-piperidin-4-yloxy]-isoquinolin-4-yl}-3-(5-pentafluoroethyl-2-p-tolyl-2H-pyrazol-3-yl)-urea mesylate | 643.0 |
| Example 37 | 1-{1-[1-(2-Fluoro-benzoyl)-piperidin-4-yloxy]-isoquinolin-4-yl}-3-[2-p-tolyl-5-(1-trifluoromethyl-cyclopropyl)-2H-pyrazol-3-yl]-urea mesylate | 673.0 |
| Example 38 | 1-{1-[1-(2,6-Difluoro-benzoyl)-piperidin-4-yloxy]-isoquinolin-4-yl}-3-[2-p-tolyl-5-(1-trifluoromethyl-cyclopropyl)-2H-pyrazol-3-yl]-urea mesylate | 691.0 |
| Example 39 | 1-{1-[1-(1-Methyl-cyclopropanecarbonyl)-piperidin-4-yloxy]-isoquinolin-4-yl}-3-[2-p-tolyl-5-(1-trifluoromethyl-cyclopropyl)-2H-pyrazol-3-yl]-urea mesylate | 633.3 |

EXAMPLE 40

1-{1-[1-(2,6-Difluoro-benzoyl)-piperidin-4-yloxy]-isoquinolin-4-yl}-3-[5-(2-fluoro-1-fluoromethyl-1-methyl-ethyl)-2-p-tolyl-2H-pyrazol-3-yl]-urea Stir 1-[5-(2-fluoro-1-fluoromethyl-1-methyl-ethyl)-2-p-tolyl-2H-pyrazol-3-yl]-3-[1-(piperidin-4-yloxy)-isoquinolin-4-yl]-urea hydrochloride (Preparation 37, 0.6 mmol, 0.3 g), 2,6-difluorobenzoyl chloride (0.6 mmol, 0.07 mL) and triethylamine (1.7 mmol, 0.2 mL) in 5 mL of dichloromethane at room temperature overnight. Add some water and extract in dichloromethane. Wash organic layer with saturated aq. sodium chloride. Dry over anhydrous sodium sulfate and concentrate under reduced pressure. Subject residue to silica gel chromatography eluting with hexanes/ethyl acetate as eluent (30%-70%). LCMS ES+(m/z) 675 [M+H].

Prepare the following compounds in a manner substantially analogous to the procedure described above.

| EXAMPLE | Compound | Data MS (ES+): m/z [M + H] |
|---|---|---|
| Example 41 | 1-[5-(2-Fluoro-1-fluoromethyl-1-methyl-ethyl)-2-p-tolyl-2H-pyrazol-3-yl]-3-{1-[1-(1-methyl-cyclopropanecarbonyl)-piperidin-4-yloxy]-isoquinolin-4-yl}-urea | 617 |
| Example 42 | 1-[5-(1,1-Bis-fluoromethyl-propyl)-2-p-tolyl-2H-pyrazol-3-yl]-3-{1-[1-(2,6-difluoro-benzoyl)-piperidin-4-yloxy]-isoquinolin-4-yl}-urea | 689 |
| Example 43 | 1-{1-[1-(2,6-Difluoro-benzoyl)-piperidin-4-yloxy]-isoquinolin-4-yl}-3-[5-(2-fluoro-1,1-dimethyl-ethyl)-2-p-tolyl-2H-pyrazol-3-yl]-urea | 657 |
| Example 44 | 1-[5-(2-Fluoro-1,1-dimethyl-ethyl)-2-p-tolyl-2H-pyrazol-3-yl]-3-{1-[1-(1-methyl-cyclopropanecarbonyl)-piperidin-4-yloxy]-isoquinolin-4-yl}-urea | 599 |

EXAMPLE 45

1-{1-[1-(2,6-Difluoro-benzoyl)-piperidin-4-yloxy]-isoquinolin-4-yl}-3-[5-(2-fluoro-1-fluoromethyl-1-methyl-ethyl)-2-p-tolyl-2H-pyrazol-3-yl]-urea mesylate Dissolve 0.13 g (0.19 mmol) of 1-{1-[1-(2,6-Difluoro-benzoyl)-piperidin-4-yloxy]-isoquinolin-4-yl}-3-[5-(2-fluoro-1-fluoromethyl-1-methyl-ethyl)-2-p-tolyl-2H-pyrazol-3-yl]-urea in dichloromethane (2 mL) and add 0.19 mL of a solution of methanesulfonic acid 1 N in dichloromethane. Evaporation of solvent under reduced pressure gives 0.09 g of the title compound as a white solid. ES+ (m/z) 675 (M+H).

Prepare the following compounds in a manner substantially analogous to the procedure described above.

<50° C. and treat with carbon (Darco G-60; 33.00 g, 2.75 moles). Stir the slurry for 30 minutes at 43-50° C., then filter over micro fiber paper and Hyflo Super Cel® (27.00 g). Seed the filtrate and allow to cool at ambient temperature during precipitation. Pack the resulting slurry in ice and stir overnight. Filter the solids, wash with THF (300.00 mL, 3.69 moles), and dry under reduced pressure at 40° C. Subject residue to silica gel chromatography eluting with 1:3 acetone/DCM, then 30% acetone in DCM to obtain 401 g (68%) 1-{1-[1-(1-methyl-cyclopropanecarbonyl)-piperidin-4-yloxy]-isoquinolin-4-yl}-3-[5-(1-methyl-cyclopropyl)-2-p-tolyl-2H-pyrazol-3-yl]-urea as a white solid $^1$H NMR (300 MHz, DMSO-$d_6$): δ 0.56 (t, J=6.0 Hz, 2H), 0.73 (t, J=6.0 Hz, 2H), 0.84 (t, J=6.0 Hz, 2H), 0.92 (t, J=6.0 Hz, 2H), 1.27 (s, 3H), 1.41 (s, 3H), 1.73-1.81 (m, 2H), 1.99-2.08 (m, 2H), 2.41 (s, 3H), 3.52-3.65 (m, 2H), 3.83-3.96 (m, 2H), 5.47-5.58 (m,

| EXAMPLE | Compound | Data MS (ES+): m/z [M + H] |
|---|---|---|
| Example 46 | 1-[5-(1,1-Bis-fluoromethyl-propyl)-2-p-tolyl-2H-pyrazol-3-yl]-3-{1-[1-(2,6-difluoro-benzoyl)-piperidin-4-yloxy]-isoquinolin-4-yl}-urea mesylate | 689 |
| Example 47 | 1-{1-[1-(2,6-Difluoro-benzoyl)-piperidin-4-yloxy]-isoquinolin-4-yl}-3-[5-(2-fluoro-1,1-dimethyl-ethyl)-2-p-tolyl-2H-pyrazol-3-yl]-urea mesylate | 657 |

EXAMPLE 48

1-{1-[1-(1-Methyl-cyclopropanecarbonyl)-piperidin-4-yloxy]-isoquinolin-4-yl}-3-[5-(1-methyl-cyclopropyl)-2-p-tolyl-2H-pyrazol-3-yl]-urea mesylate Add [4-(4-Amino-isoquinolin-1-yloxy)-piperidin-1-yl]-(1-methyl-cyclopropyl)-methanone (Preparation 23, 331.00 g, 1.02 moles), THF (3.97 L, 48.79 moles), [5-(1-Methyl-cyclopropyl)-2-p-tolyl-2H-pyrazol-3-yl]-carbamic acid 2,2,2-trichloro-ethyl ester (Preparation 18, 410.00 g, 1.02 moles), and DIPE (159.00 g, 1.22 moles) to a 12 L Morton flask equipped with overhead stirrer, thermocouple, and reflux condenser. Reflux the mixture for 22 hours. Cool reaction to 1H), 6.22 (s, 1H), 7.37 (d, J=8.1 Hz, 2H), 7.44 (d, J=8.1 Hz, 2H), 7.65-7.71 (m, 1H), 7.78-7.83 (m, 2H), 8.12 (s, 1H), 8.27 (d, J=8.4 Hz, 1H), 8.58 (s, 1H), 8.69 (s, 1H).

Charge the free base (400.00 g, 6.91 moles) and dichloromethane (3.00 L, 46.80 moles) to a 5 L flask equipped with overhead stirrer. Add methanesulfonic acid (72.00 g, 7.49 moles) dropwise at room temperature. Stir the reaction for 1 hour. Filter and remove solvent under reduced pressure. Add diethyl ether (4 L) and stir overnight. Filter and dry under reduced pressure to obtain the title compound, 467.8 g. $^1$H NMR (DMSO-$d_6$): δ 0.52 (t, J=2.5 Hz, 2H), 0.70 (t, J=2.5 Hz, 2H), 0.80 (t, J=2.5 Hz, 2H), 0.90 (t, J=2.5 Hz, 2H), 1.24 (s, 3H), 1.38 (s, 3H), 1.76 (br, 2H), 2.02 (br, 2H), 2.38 (s, 3H), 2.40 (s, 3H), 3.55 (br, 2H), 3.85 (br, 2H), 5.49 (m, 1H), 6.20

(s, 1H), 7.34 (d, J=8.5 Hz, 2H), 7.42 (d, J=8.5 Hz, 2H), 7.64 (dd, J=8.5 Hz, 1H), 7.77 (s, 1H), 7.79 (s, 1H), 8.08 (s, 1H), 8.24 (d, J=8.5 Hz, 1H), 8.62 (s, 1H), 8.72 (s, 1H).

EXAMPLE 49

1-[5-(1-Fluoromethyl-cyclopropyl)-2-p-tolyl-2H-pyrazol-3-yl]-3-{1-[1-(1-methyl-cyclopropanecarbonyl)-piperidin-4-yloxy]-isoquinolin-4-yl}-urea mesylate

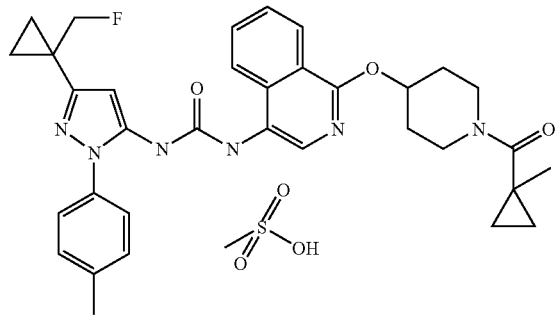

Add 5-(1-fluoromethyl-cyclopropyl)-2-p-tolyl-2H-pyrazol-3-ylamine (160.00 mg; 652.26 μmoles) dissolved in 1 L of DCM slowly to a solution of 1,1'-carbonyldiimidazole (158.65 mg, 978.39 μmoles) in DCM. Stir mixture at 40° C. for 7 hours. Then add a solution of [4-(4-Amino-isoquinolin-1-yloxy)-piperidin-1-yl]-(1-methyl-cyclopropyl)-methanone (Preparation 23, 212.25 mg, 652.26 μmoles, 1.00 equiv) in 1 mL of DCM. Stir mixture overnight. Evaporate solvent under $N_2$. Purify first by HLB cartridge (6 g) using $NH_4CO_3$/MeOH (100:0 to 0:100) and then finally by HPLC (Kromasil C18 column (100×21.2 mm, 5 □m (Hi-Chrom). The mobile phase is water (solvent A) and acetonitrile (solvent B), both containing 0.05% trifluoroacetic acid (TFA). Gradient mode: 2 min at 40% of B, from 40 to 60% of B in 6 min. Finally, 2 min at 95% of B. Flow rate: 25 mL/min) affording 1-[5-(1-fluoromethyl-cyclopropyl)-2-p-tolyl-2H-pyrazol-3-yl]-3-{1-[1-(1-methyl-cyclopropanecarbonyl)-piperidin-4-yloxy]-isoquinolin-4-yl}-urea as a solid (19 mg, 5% yield). ES+ (m/z):597[M+1].

Add methanesulfonic acid 1 M (30.17 μmoles; 30.17 μL) to a solution of 1-[5-(1-fluoromethyl-cyclopropyl)-2-p-tolyl-2H-pyrazol-3-yl]-3-{1-[1-(1-methyl-cyclopropanecarbonyl)-piperidin-4-yloxy]-isoquinolin-4-yl}-urea (18.00 mg, 30.17 μmoles) in 0.5 mL of Dichloromethane. Stir the mixture at room temperature for 1 hour. Evaporate solvent under nitrogen to afford the title compound as a solid (20 mg, 96% yield). ES+ (m/z): 597.4 [M+1]

Inhibition of p38 Kinase

Standard Solution Preparations

The kinase buffer solution is prepared by combining 2.5 mL 1M Tris-HCl (pH 7.5), 0.1 mL 1 M dithiothreitol, 1.0 mL 1 M magnesium chloride, and 300 μL 1% Triton X-100 and diluting to 100 mL with water. 84 mL of this kinase buffer solution is combined with 16 mL DMSO to prepare the 16% DMSO solution.

The 200 μM ATP solution is prepared by adding 102.6 μL 10 mM aqueous ATP, 25 μL $^{33}$P-ATP, and 163.5 μL of 4 mM aqueous Epidermal Growth Factor Peptide 661-681 (Biomol, Catalog #P-121) in 5 mL kinase buffer solution.

The p38 kinase enzyme solution is prepared by dissolving 9.5 μL concentrated enzyme solution (250 ng p38 enzyme/μL kinase buffer solution) in 1536 μL kinase buffer solution.

Sample Preparation

An 80 μM solution of each test compound and control compound are prepared by dissolving 2 μL of a 10 mM stock solution of the respective compounds in dimethylsulfoxide in 248 μL of the 16% DMSO solution in a Costar 96-well microtiter plate. The plate is placed onto the Tecan Genesis automated liquid handler for 1:3 serial dilutions.

Assay

10 μL of serially diluted compound is placed with a Beckman Multimek 96-well automated liquid handler to the assay plate. 20 μL of 200 μM ATP solution is added with a Titertek Multidrop 8-channel liquid handler. 10 μL of p38 kinase enzyme solution is transferred to the assay plate using the Multimek. The mixture is allowed to react for 40 minutes at 30° C. and then the reaction is stopped by adding 60 mL of freshly prepared 5% glacial AcOH with Multidrop. 80 μL of this solution is transferred to an "MAPH" plate using the Multimek. The plates are allowed to set for 30 minutes at room temperature and then washed/aspirated on the Titertek MAP extractor with freshly prepared 0.5% glacial AcOH (1×300 μL, 2×200 μL). The plates are blotted and 100 μL MicroScint-20 scintillation fluid (Packard Bioscience) is added with the Multidrop. The plates are allowed to sit for 30 min and counted on a PE/Wallac Microbeta Trilux scintillation counter for $^{33}$P-isotope.

The compound exemplified in Example 12 is initially tested at 10 concentrations (20 μM-1 nM using 1:3 serial dilutions). Compounds with $IC_{50}$ values less than 25 nM are re-tested at a starting concentration of 2 μM to 0.1 nM (1:3 serial dilutions). $IC_{50}$ values are calculated (IDBS Activity-Base software) for each compound using non-linear regression. Example 12 is tested essentially as described above and is found to inhibit the p38 kinase enzyme with an $IC_{50}$ of 34 nM.

Inhibition of p-MAPKAPK2 In Vitro

RAW 264.7 cells (a murine monocytic/macrophage line ATCC) are seeded at a density of 50,000 cells/well in 96-well plates with RPMI-1640 medium plus 10% fetal bovine serum (FBS) and allowed to settle and adhere to the bottom of the well for 48 hours. After reaching confluence, cells are treated for 2 hours with 10 serial dilutions of different compounds. A control compound is always included. After 2 hours, anisomicin (100 ug/ml) is added and cells are incubated for 30 minutes at 37° C. under a 5% $CO_2$ atmosphere. Then, cells are fixed and treated with hydrogen peroxide in order to remove endogenous peroxidase. Finally, plates are blocked with FBS, washed, and an ELISA assay is carried out by using an antiphospho-MAPKAPK2 (Thr 334, Cell Signalling, Cat # 3041) antibody and ahP-Conjugated Secondary Antibody. This reaction is detected by using FEMTO (Pierce) which is an enhanced chemiluminiscent substrate ahP that results in rapid kinetic light output and high signal intensity. The compound exemplified in Example 12 is tested essentially as described above and is found to inhibit the pMAPKAPK2 enzyme production with an $IC_{50}$ of 7 nM.

The exemplified compounds were tested essentially as described above and were found to have $IC_{50}$ values less than or equal to 200 nM. The following compounds were tested essentially as described above and were found to have the following activity:

| EXAMPLE | IC$_{50}$ (nM) |
|---------|----------------|
| 1 | 44 |
| 3 | 25 |
| 9 | 101 |
| 23 | 125 |

Inhibition of TNFα In Vitro

Mouse Peritoneal Macrophages 1 mL thioglycolate broth (5.0 g yeast extract, 15.0 g casitone or trypticase, 5.0 g dextrose, 2.5 g sodium chloride, 0.75 g L-cystine, 0.5 g sodium thioglycolate, 1.0 mg resazurin, and 0.75 g agar in 1.0 L distilled water) are injected into the peritoneal cavity of Balb/C female mice. At day 4 or 5 post-injection the mice are sacrificed and then injected i.p. with 4 mL RPMI-1640 medium (BioWhittaker) and the peritoneal macrophages are withdrawn by syringe.

Cytokine Production

Mouse peritoneal macrophages are counted with a hemocytometer and adjusted to 5×10$^5$ cells/well in 96-well plates in RPMI-1640 medium with 10% fetal bovine serum. 200 μL/well is plated in 96-well plates and the cells allowed to settle and adhere to the bottom of the well for at least 3 hours. The test compound or standard p38 kinase inhibitor is pre-treated using a series of 8 concentrations for 1 hour at 37° C. (20 μL/well). The cells are treated with a mixture of 50 ng/mL lipopolysaccharide (LPS) and 10 U/mL interferon-γ for 18 hours at 37° C. (20 μL/well). The conditioned media is harvested and assayed for TNFα production using the Luminex detection procedure.

TNFα/Luminex Detection Assay (Bio-Rad Bio-Plex Kit—Catalog #171-G12221)

The lyophilized premixed TNFα standard (1 standard tube/two 96-well plates) is reconstituted with 50 μL sterile water (500,000 pg/mL). The samples are vortexed for 5 seconds, incubated on ice for 30 minutes, and vortexed for 5 seconds before use. A set of twelve 1.5 mL tubes are labeled with #1-thru #12 and then the amounts of cell media shown below added to the appropriate tubes (standard concentrations are as follows: 50,000; 25,000; 12,500; 6,250; 3,125; 1,562.5; 781.3; 390.6; 195.3; 97.7; 48.8; and 24.4 pg/mL). The pre-mixed anti-cytokine conjugated beads are vortexed (25×) vigorously for 30 seconds. The anti-cytokine conjugated beads are diluted to a 1× concentration using 1× Bio-Plex Assay Buffer. For every plate, 240 μL of the pre-mixed beads is added to 5760 μL of Bio-Plex Assay Buffer. A Millipore 96-well filter plate is blocked with 100 μL/well of blocking buffer. The blocking buffer is filtered through using a Millipore filtration system and then toweled dry. 2 washes are performed on the filter plate with 100 μl/well of Bio-Plex Assay Buffer and toweled dry. The 1× anti-cytokine conjugated beads are vortexed for 15 seconds and added 50 μL to each well. This is filtered through and toweled dry. 2 washes are performed on plates with 100 μL/well of Bio-Plex Wash Buffer. Again, it is filtered through and toweled dry. 50 μL of sample or standard is added to each sample well. This is incubated for 60 seconds at room temperature on a shaker protected from light at setting 6 and then for 30 min at setting 3 and then placed in the refrigerator overnight. 3 washes are performed with Bio-Plex Wash Buffer. Filter through and toweled dry. The cytokine detection antibody is prepared (~10 min prior to use) for every plate and 60 μL of the premixed cytokine detection antibody stock is added to 5940 μL of Bio-Plex Detection Antibody Diluent.

50 μL of cytokine detection antibody is added and incubated for 60 seconds at room temperature on a shaker protected from light at setting 6 and then for 30 minutes at setting 3. 3 washes are performed with the Bio-Plex Wash Buffer. This is filtered through and toweled dry. Strept-PE (~10 minutes prior to use) is prepared for every plate and 60 μL to 5940 μL of Bio-Plex Assay Buffer added. 50 μL of Streptavidin-PE is added to each well and incubated for 60 seconds at room temperature on a shaker protected from light at setting 6 and then for 10 minutes at setting 3. 3 washes are performed with Bio-Plex Wash Buffer. This is filtered through. The beads are re-suspended in 100 μL/well of Bio-Plex Assay Buffer. Standards and samples are read on a Luminex machine. These intensity readings are then converted to picogram/milliliter units based on a 12-point standard curve created in duplicate using a four-parameter logistic regression method (Bio-Plex Manager 2.0, Bio-Rad), and the IC$_{50}$ calculated.

The compound exemplified in Example 12 is tested essentially as described above and suppressed TNFα in vitro with an IC$_{50}$ less than 9 nM.

Inhibition of TNFα in vivo

Compounds are administered p.o. (30, 10, 3 and 1 mg/kg) to female Balb/c mice (6 mice/dose). 1 hour following compound administration at 4 doses (P.O. at volume of 0.1 mL/mouse; vehicle: 1% NaCMC/0.25% Tween-80 in water); mice are given an IP-injection of LPS at 400 μg/kg. 1.5 hours after LPS challenging, mice are anesthetized with isoflurane and blood is taken via cardiac puncture. TNFa-levels in the plasma are determined using ELISA kit from R&D Systems and dose response ED50 is determined.

The compound exemplified in Example 12 is tested essentially as described above and suppressed TNFα in vivo with an TMED50 of 1.0 mg/kg. The Threshold Minimum Effective Dose (TMED) 50 is the dose at which greater than or equal to 50% inhibition was achieved and statistically different from control/placebo.

Oral Exposure

Compounds are screened for oral exposure in male Fischer 344 rats. Animals are fasted overnight and administered test compounds prepared as suspensions in sodium carboxymethylcellulose (1% w/v) containing Tween 80 (0.25% v/v) and antifoam (0.1% w/v). Dose suspensions are prepared at 1 mg/mL and administered at 1 mL/kg by gavage. Blood samples are taken between 0.5 h and 7 h after dose administration and plasma are prepared by centrifugation. Plasma samples are analyzed using online solid phase extraction and LC/MS/MS.

The compound exemplified in Example 12 is tested essentially as described above and the Cmax is 9390 ng/mL with an AUC (0-7 h) of 36800 ng.h/mL.

Effect on Intra-Articular LPS Induced TNFα

Intra-articular injection of LPS into rat ankles induces the synthesis of TNFα, which can be measured in synovial lavage fluid. High levels of TNFα are detectable within 2 hours. Since the joint is the site where arthritis develops, this model can rapidly determine whether an orally administered compound has an effect on an inflammatory response in the synovium.

Six female Lewis rats (150-200 g) are place in each treatment group. The animals are given vehicle (1% NaCarboxylmethylcellulose-0.25% Tween 80) or test compound (1 mg/kg, 3 mg/kg, 10 mg/kg, and 30 mg/kg) orally. One hour later, 10 µl LPS (10 µg) is administered intra-articularly into the right ankle of each rat, while the left ankle receives 10 µL of saline. After two hours, each ankle is lavaged with 100 µL of saline. The lavage is collected and stored at −80° C.

Group#1: Vehicle (1%/NaCMC-0.25% Tween 80, 1 mL, PO)
Group#2: Test compound (1 mg/kg, 1 mL, PO)
Group#3: Test compound (3 mg/kg, 1 mL, PO)
Group#4: Test compound (10 mg/kg, 1 mL, PO)
Group#5: Test compound (30 mg/kg, 1 mL, PO)

TNFα is measured with a commercially available ELISA kit (R&D, RTA00). Treatment with the compound exemplified in Example 12 produces a dose response inhibition of TNFα synthesis, as measured in the synovial lavage fluid with a TMED50=2.54 mg/kg.

Anisomycin-Stimulated Mice Ex-Vivo
Phospho-MAPKAPK2 Inhibition Assay by Flow Cytometry Female Balb/c mice with 8-10 week-old age are purchased from Taconic Inc. and dosed po with 0.2 mL volume of compounds at the concentrations of 30, 10, 3, 1 mg/kg. Blood is obtained from cardiac puncture after 2 hours or other indicated time periods and collected in EDTA-containing tubes. 100 µL of blood is incubated at 37° C. for 10 minutes. Whole blood is then mixed with FITC-conjugated rat anti-mouse Ly-6G mAb (1:250) and APC-conjugated rat anti-mouse CD11b mAb (1:100) and stimulated with 10 µg/ml anisomycin. Both cell surface antigen staining and anisomycin stimulation is conducted at 37° C. for 15 min and followed up with Lyse/Fix buffer (BD Biosciences, Cat# 558049) for 10 min at room temperature. Lysed blood samples are spun down at 600×g for 8 minutes at room temperature with additional wash once by 4 mL PBS. 200 µL of diluted anti-Phospho-MAPKAPK-2 (Thr334) antibody (1:100 dilution) (Cell Signaling, Cat# 3041) and mouse BD Fc Block (1:100 dilution) (BD Biosciences, 553141) in permeabilization Medium B (Caltag, Cat# GAS002S-5) are added into blood cells and incubate at room temperature for 30 min. After the incubation, 3 mL of stain/wash buffer is added and cells are spanned down as described above with additional wash with 3 ml stain/wash buffer. Cells are then subjected to flowcytometry assay using Beckman Coulter F500. Mean fluorescence of phosphono-MapKap-K2 staining is measured on gated CD11b+Ly6G-cells. Data analysis is performed by JMP program. Treatment with the compound exemplified in Example 12 produces a dose response inhibition of p-MAPKAPK2 synthesis with TMED50=2.20 mg/kg Rat Collagen Induced Arthritis Efficacy Model Female Lewis rats (≅190 g, Charles River Labs) are immunized with Bovine type II collagen (2 mg/mL) emulsified with an equal volume of adjuvant (aluminum hydroxide). The rats are immunized with approximately 0.3 mg of the emulsion intradermally on the back near the base of the tail. All animals are re-immunized 7 days later according to the same protocol. The rats begin to develop arthritis (characterized by swelling and redness of one or both ankles) from 12 to 14 days after the first immunization. The rats are equally distributed into five treatment groups at the first signs of arthritis and treatment is initiated with each rat dosed bid for 14 days.

Treatment Groups:
Group 1 Vehicle (1% NaCarboxymethylcellulose+0.25% Tween 80) 1 mL, PO, Bid×14 days
Group 2 Test compound, 5 mg/kg, 1 mL, PO, Bid×14
Group 3 Test compound, 15 mg/kg, 1 mL, PO, Bid×14
Group 4 Test compound, 30 mg/kg, 1 mL, PO, Bid×14
Group 5 Prednisolone 10 mg/kg, 1 mL, PO, qd×14

Ankle diameter is measured with calipers 5 days a week and recorded. Data is expressed as the area under the curve (AUC) generated from the composite inflammation scores and statistical analysis performed.

Oral administration of the compound of the present invention is preferred. However, oral administration is not the only route or even the only preferred route. For example, transdermal administration may be very desirable for patients who are forgetful or petulant about taking oral medicine, and the intravenous route may be preferred as a matter of convenience or to avoid potential complications related to oral administration. Compounds of Formula I may also be administered by the percutaneous, intramuscular, intranasal or intrarectal route in particular circumstances. The route of administration may be varied in any way, limited by the physical properties of the drugs, the convenience of the patient and the caregiver, and other relevant circumstances (*Remington's Pharmaceutical Sciences,* 18th Edition, Mack Publishing Co. (1990)).

The pharmaceutical compositions are prepared in a manner well known in the pharmaceutical art. The carrier or excipient may be a solid, semi-solid, or liquid material that can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

The compound of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations of the present invention may be determined by methods well known to the skilled artisan.

The tablets, pills, capsules, troches, and the like may also contain one or more of the following adjuvants: binders such as povidone, hydroxypropyl cellulose, microcrystalline cellulose, or gelatin; excipients or diluents such as: starch, lactose, microcrystalline cellulose or dicalcium phosphate, disintegrating agents such as: croscarmellose, crospovidone, sodium starch glycolate, corn starch and the like; lubricants such as: magnesium stearate, stearic acid, talc or hydrogenated vegetable oil; glidants such as colloidal silicon dioxide; wetting agents such as: sodium lauryl sulfate and polysorbate 80; and sweetening agents such as: sucrose, aspartame or saccharin may be added or a flavoring agent such as: peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, as coatings. Thus, tablets or pills may be coated with sugar, hydroxypropyl methylcellulose, polymethacrylates, or other coating agents. Syrups may contain, in addition to the present compounds, sucrose as a sweetening agent and certain preservatives, dyes and colorings and flavors. Materials used in preparing these various compositions should be pharmaceutically pure and non-toxic in the amounts used. A preferred formulation is prepared by adding 10% N-methylpyrrolidone to the desired dose of a compound of Formula I, followed by the addition of a solution consisting of 20% hydroxypropyl-beta-cyclodextrin, 5% methylcellulose, 0.5% antifoam, and HCl 0.01N, w/w %.

The compounds of Formula I are generally effective over a wide dosage range. For example, dosages per day normally fall within the range of about 0.0001 to about 30 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

The invention claimed is:

1. A compound of Formula I:

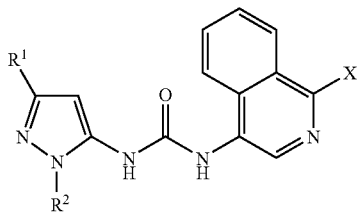

where:
X is selected from the group consisting of

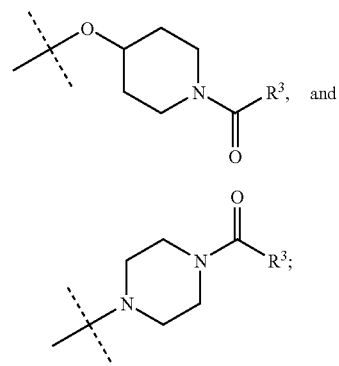

$R^1$ is $C_1$-$C_4$ alkyl, $C_3$-$C_4$ cycloalkyl optionally substituted with one or two substituents selected from the group of $C_1$-$C_4$ alkoxy, methyl, and trifluoromethyl; or $C_1$-$C_4$ alkylhalo;

$R^2$ is phenyl optionally substituted with $C_1$-$C_4$ alkyl, or pyridinyl optionally substituted with $C_1$-$C_4$ alkyl;

$R^3$ is amino, $C_1$-$C_4$ alkyl, $C_1$-$C_4$ alkoxy, $C_1$-$C_4$ alkylhalo, $C_3$-$C_4$ cycloalkyl optionally substituted with a substituent selected from methyl, trifluoromethyl, or halo; phenyl or thienyl each optionally substituted with a first substituent selected from the group consisting of: halo, $C_1$-$C_4$ alkyl, and $C_1$-$C_4$ alkoxy, and optionally further substituted with a second substituent selected from halo; or a pharmaceutically acceptable salt thereof.

2. A compound of claim 1 where X is

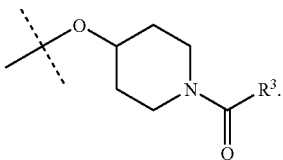

3. A compound of claim 1 where $R^2$ is 4-tolyl.

4. A compound of claim 1 where $R^1$ is 1-methyl-1-cyclopropyl, 2-fluoro-1,1-dimethyl-ethyl, or 2-fluoro-1-fluoromethyl-1-methyl-ethyl.

5. A compound of claim 1 where $R^3$ is 1-methyl-1-cyclopropyl.

6. A compound of Formula I:

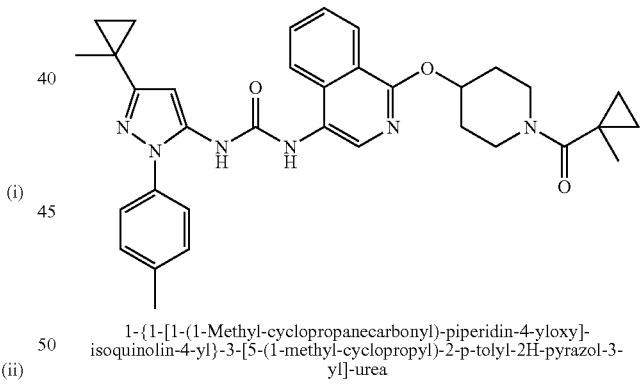

1-{1-[1-(1-Methyl-cyclopropanecarbonyl)-piperidin-4-yloxy]-isoquinolin-4-yl}-3-[5-(1-methyl-cyclopropyl)-2-p-tolyl-2H-pyrazol-3-yl]-urea or a pharmaceutically acceptable salt thereof.

7. A pharmaceutical formulation comprising a compound of claim 1 in combination with a pharmaceutically acceptable excipient, carrier, or diluent.

* * * * *

UNITED STATES PATENT AND TRADEMARK OFFICE
CERTIFICATE OF CORRECTION

PATENT NO.       : 7,582,638 B2                                     Page 1 of 1
APPLICATION NO.  : 12/089420
DATED            : September 1, 2009
INVENTOR(S)      : Alfonso De Dios et al.

It is certified that error appears in the above-identified patent and that said Letters Patent is hereby corrected as shown below:

On title page
1) Page 1, PCT Publication Date:
   Delete "Oct. 5, 2007" and
   Insert --May 10, 2007--, therefore.

2) Page 1, Column 2, Abstract:
   Delete "R1, R2" and
   Insert --$R^1$, $R^2$, --, therefore.

Signed and Sealed this
Fourteenth Day of June, 2011

David J. Kappos
*Director of the United States Patent and Trademark Office*